United States Patent [19]

Scheller et al.

[11] Patent Number: 5,157,603
[45] Date of Patent: * Oct. 20, 1992

[54] CONTROL SYSTEM FOR OPHTHALMIC SURGICAL INSTRUMENTS

[75] Inventors: Gregg D. Scheller, Ballwin; R. Bruce Lucas, University City; Gideon Yefet, St. Louis, all of Mo.; David Dallam, Pittsford, N.Y.

[73] Assignee: Storz Instrument Company, St. Louis, Mo.

[*] Notice: The portion of the term of this patent subsequent to Jun. 12, 2007 has been disclaimed.

[21] Appl. No.: 438,863

[22] Filed: Nov. 20, 1989

Related U.S. Application Data

[60] Division of Ser. No. 267,713, Nov. 10, 1948, Pat. No. 4,933,843, which is a continuation of Ser. No. 928,170, Nov. 6, 1986, abandoned.

[51] Int. Cl.[5] .............................................. G06F 15/42
[52] U.S. Cl. .................................. 364/413.01; 604/22; 604/66; 604/67; 364/188
[58] Field of Search ............... 364/413.01, 138, 146, 364/474.11, 188; 604/22, 65, 66, 67; 606/4

[56] References Cited

U.S. PATENT DOCUMENTS

| | | | |
|---|---|---|---|
| 3,589,363 | 6/1971 | Banko et al. | 604/22 |
| 3,693,613 | 9/1972 | Kelman | 606/169 |
| 3,812,855 | 5/1974 | Banko | 604/31 |
| 3,920,014 | 11/1975 | Banko | 604/31 |
| 3,930,505 | 1/1976 | Wallach | 604/22 |
| 4,019,514 | 4/1977 | Banko | 604/31 |
| 4,024,866 | 5/1977 | Wallach | 604/31 |
| 4,156,187 | 5/1979 | Murry et al. | 324/142 |
| 4,168,707 | 9/1979 | Douvas et al. | 604/32 |
| 4,180,074 | 12/1979 | Murray et al. | 604/31 |
| 4,395,258 | 7/1983 | Wang et al. | 604/65 |
| 4,428,748 | 1/1984 | Peyman et al. | 604/22 |
| 4,432,360 | 2/1984 | Mumford et al. | 128/419 PG |
| 4,457,750 | 7/1984 | Hill | 604/65 |
| 4,493,698 | 1/1985 | Wang et al. | 604/51 |
| 4,508,532 | 4/1985 | Drews et al. | 604/22 |
| 4,529,401 | 7/1985 | Leslie et al. | 604/131 |
| 4,553,958 | 11/1985 | Le Cocq | 604/67 |
| 4,557,270 | 12/1985 | John | 128/731 |
| 4,564,018 | 1/1986 | Hutchison et al. | 128/661.06 |
| 4,580,557 | 4/1986 | Hertzmann | 606/12 |
| 4,622,503 | 11/1986 | Sandblom et al. | 318/645 |
| 4,626,248 | 12/1986 | Scheller | 604/319 |
| 4,642,769 | 2/1987 | Petrofsky | 364/413.27 |
| 4,650,460 | 3/1987 | Roizenblatt | 604/22 |
| 4,669,466 | 6/1987 | L'Esperance | 606/3 |
| 4,676,776 | 6/1987 | Howson | 604/31 |
| 4,688,574 | 8/1987 | Dufresne et al. | 128/421 |
| 4,695,954 | 9/1987 | Rose et al. | 364/413.01 |
| 4,706,687 | 11/1987 | Rogers | 128/752 |
| 4,722,350 | 2/1988 | Armeniades et al. | 128/748 |
| 4,757,814 | 7/1988 | Wang et al. | 606/174 |
| 4,758,220 | 7/1988 | Sundblom et al. | 604/65 |
| 4,768,506 | 9/1988 | Parker et al. | 606/174 |
| 4,770,654 | 9/1988 | Rogers et al. | 604/22 |
| 4,798,580 | 1/1989 | DeMeo et al. | 604/30 |

OTHER PUBLICATIONS

Signals, "Smart Cards—The New Bank Cards", Macmillan Publishing Co. @1985, pp. 5-7 & 101-104.
Brochure: "SITE 54 KHz . . . " (page 4, 1988).
"1989 Guide to Phacoemulsification Units", Ophthalmology Times, pp. 30-32 (Feb., 1989).

(List continued on next page.)

Primary Examiner—Joseph L. Dixon
Assistant Examiner—Allen M. Lo
Attorney, Agent, or Firm—Brooks & Kushman

[57] ABSTRACT

The control system is programmable by the user by inserting a preprogrammed key into the system console. The key changes the default values normally used by the control system to those values selected by a particular surgeon. The control console thus emulates the performance characteristics of a wide variety of different types of microsurgical control systems, leaving the surgeon free to perform the operation without having to adjust to a new or unfamiliar system. The display screen is self-illuminating and provides a plurality of control menus generated by data stored in computer memory circuits. By bank switching the memory circuits, the display can be caused to appear in a wide variety of different languages.

4 Claims, 21 Drawing Sheets

OTHER PUBLICATIONS

Site TXR Product Catalog (page 21, Copyright 1985).

Surgical Design Corp., product brochure entitled "Setting the Standard in Intraocular Microsurgery" (page 16, copyright 1986).

Storz product brochure entitled "System 20 Ophthalmic Surgical System" (page 4, undated).

"Site 54 KHz Linear Pulse Phaco Module" product brochure (page 4, undated).

Site TXR product brochure entitled "The first totally modular ophthalmic microsurgical system" (page 9, undated).

Allergan Medical Optics product brochure entitled "The AMO commitment to a Small Incision begins here . . . " (page 6, Copyright 1987).

Steve Charles and Carl Wang, "A Linear Suction Control for the Vitreous Cutter (Ocutome)" *Arch Ophthalmol,* vol. 99, page 1613, Sep. 1981.

CooperVision brochure entitled "You Demand Versatility, We Deliver System Six" (page 1, undated).

Brochure entitled "Fresh Idea Your Custom Surgical Center CooperVision System VI" (page 6, Copyright 1983).

Cavitron/Kelman Model 6500 A.I.s & Model 7500 I/A System (page 6, Copyright 1983).

Grieshaber & Co., "MPC Membrane Peeler Cutter" product brochure (pages 2, 1980).

OMS brochure "The System Solution, It Can Be Very Convincing" (8 pp., undated).

MVS XIV, XII, XX brochure (page 4, undated).

CooperVision Brochure "The Cutting Edge of Ultrasonic Technology", (2 pp., 1986).

Brochure: Cavitron/Kelman Phaco-Emulsifier Aspirator Model 8001 (page 2, 1985).

Brochure: Cavitron/Kelman Phaco-Emulsifier Aspirator, Model 9001 (page 2, 1985).

Advertisement: "Set your Site on Extra Cap Surgery" (page 1, undated).

Brochure: "Surgical Design" (page 6, undated).

Brochure: "Storz Irrigation Aspiration System" (page 12 1983); and Instruction Manual (page 9).

Brochure: "Storz MicroVit Vitrectomy System" (page 4 with flap, 1983); and Instruction Manual (page 18).

Brochure: "Introducing PHACO PLUS" (page 2, undated).

Book: Charles, "Vitreous Microsurgery", Ch. 2 (page 21, 1987).

Article: Wang and Charles, "Microsurgical Instrumentation For Vitrectomy: Part 1", Journal of Clinical Engineering (page 8, 1983).

Storz MicroVit Vitrectomy System Instruction Manual (page 20, undated).

United Surgical Corp., "Phacotron Plus" pamphlet (page 1, undated).

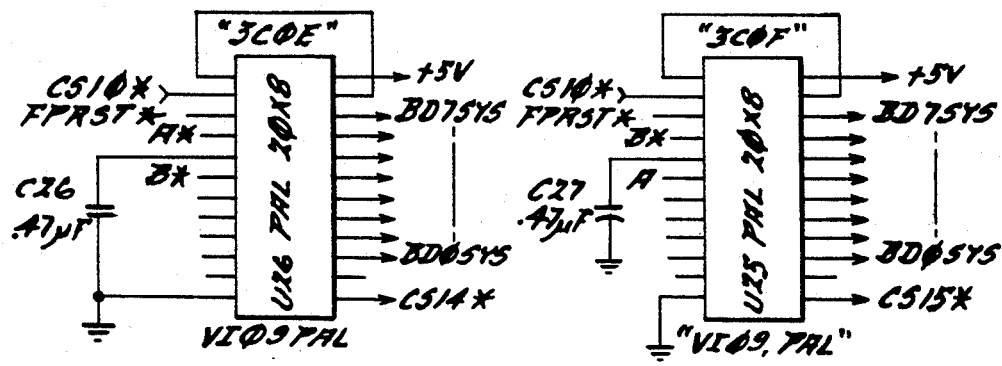
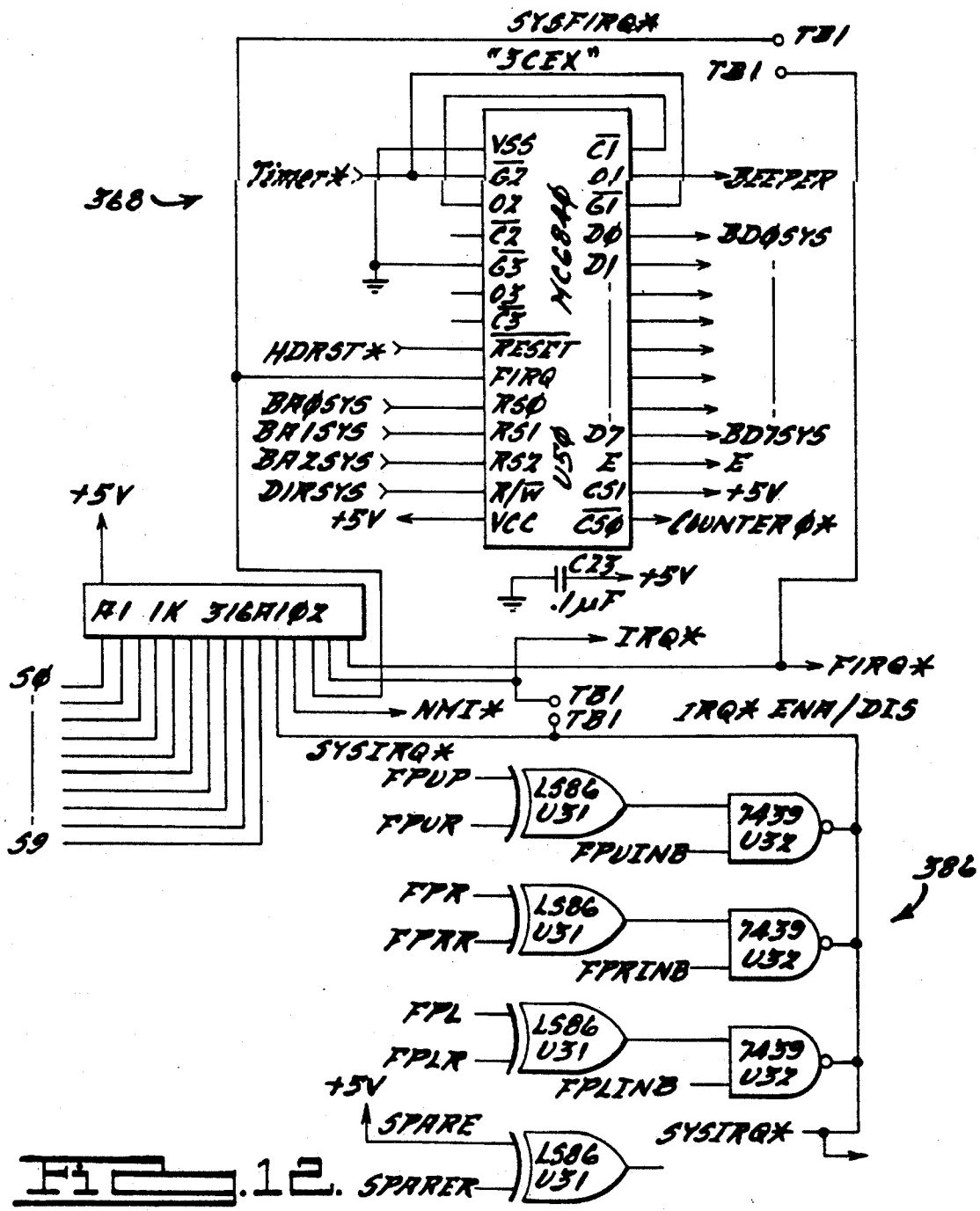
FIG. 12.

CONTROL SYSTEM FOR OPHTHALMIC SURGICAL INSTRUMENTS

This is a division of co-pending application Ser. No. 267,713 filed on Nov. 4, 1988, now U.S. Pat. No. 4,933,843 which was a continuation of Ser. No. 928,170 filed on Nov. 6, 1986, now abandoned.

MICROFICHE APPENDIX

This application includes a microfiche appendix having one microfiche and thirty-six frames.

BACKGROUND AND SUMMARY OF THE INVENTION

The present invention relates generally to microsurgical and ophthalmic systems and more particularly to a programmable control system and console for operating microsurgical instruments.

Present day ophthalmic microsurgical systems provide one or more pneumatically operated (fluid pressure operated) surgical instruments connected to a control console. The control console provides the fluid pressure signals for operating the instruments and usually includes several different types of human actuable controllers for controlling the fluid pressure signals supplied to the surgical instruments. Usually included is a foot pedal controller which the surgeon can use to control a surgical instrument.

The conventional console also has push button switches and adjustable knobs for setting the desired operation characteristics of the system. The conventional control system usually serves several different functions. For example, the typical ophthalmic microsurgical system has both anterior and posterior segment capabilities and may include a variety of functions, such as irrigation/aspiration, vitrectomy, microscissor cutting, fiber optic illumination, and fragmentation/emulsification.

While conventional microsurgical systems and ophthalmic systems have helped to make microsurgery and ophthalmic surgery possible, these systems are not without drawbacks. Microsurgical and ophthalmic systems are relatively costly and are often purchased by hospitals and clinics for sharing among many surgeons with different specialities. In eye surgery, for example, some surgeons may specialize in anterior segment procedures, while other surgeons may specialize in posterior segment procedures. Due to differences in these procedures, the control system will not be set up in the same manner for both. Also, due to the delicate nature of this type of surgery, the response characteristics or "feel" of the system can be a concern to surgeons who practice in several different hospitals, using different makes and models of equipment. It would be desirable to eliminate the differences in performance characteristics between one system and the next, while at the same time providing enough flexibility in the system to accommodate a variety of different procedures. The prior art has not met these objectives.

The present invention greatly improves upon the prior art by providing a programmable and universal microsurgical control system, which can be readily programmed to perform a variety of different surgical procedures and which may be programmed to provide the response characteristics which any given surgeon may require. The control system is preprogrammed to operate in a variety of different modes to provide a variety of different procedures. These preprogrammed modes can be selected by pressing front panel buttons.

In addition to the preprogrammed modes, each surgeon can be provided with a programming key, which includes a digital memory circuit loaded with particular response characteristic parameters and particular surgical procedure parameters selected by that surgeon. By inserting the key into the system console jack, the system is automatically set up to respond in a familiar way to each surgeon.

For maximum versatility, the console push buttons and potentiometer knobs are programmable. Their functions and response characteristics can be changed to suit the surgeons' needs. An electronic display screen on the console displays the current function of each programmable button and knob as well as other pertinent information. The display screen is self-illuminating so that it can be read easily in darkened operating rooms.

More specifically, the microsurgical control system of the invention is adapted for controlling fluid pressure controlled microsurgical instruments. The term "fluid pressure", unless otherwise specified, includes both positive pressure and negative pressure (vacuum), as well as pneumatic implementations. The microsurgical control system comprises a means for providing fluid pressure couplable to the microsurgical instrument for delivering a fluid pressure signal to the instrument. A manually actuable controller is coupled with the means for providing fluid pressure for adjusting the fluid pressure signal in response to human actuation. A digitally programmed electronic circuit coupled to the controller selectively alters the manner in which the controller responds to human actuation.

Further, in accordance with the invention, the microsurgical control system includes a console and means on the console for connecting to at least one microsurgical instrument. The console has an electronic display screen and a plurality of manually actuable controllers disposed thereon at locations corresponding to predetermined regions of the display screen. The system includes a menu generating means coupled to the display screen for writing predetermined human readable messages at the predetermined regions of the display screen. A procedure control means is coupled to the connecting means for defining and providing a plurality of predetermined and selectable surgical procedures for controlling the instrument. A procedure selection means is coupled to the procedure control means and is responsive to the human actuable controller, for causing the procedure control means to perform a selected one of the plurality of procedures.

Still further in accordance with the invention, the control means includes a means for defining predetermined and selectable surgical procedures. The defining means includes a jack on the console and at least one memory circuit removably connected to the jack, for storing parameters used to define the surgical procedures.

For a more complete understanding of the invention, its objects and advantages, reference may be had to the following specification and to the accompanying drawings.

BRIEF DESCRIPTION OF THE DRAWINGS

FIG. 12 is a detailed schematic diagram illustrating the interrupt request handling circuitry of the electronic control system;

DESCRIPTION OF THE PREFERRED EMBODIMENT

Figure 1:
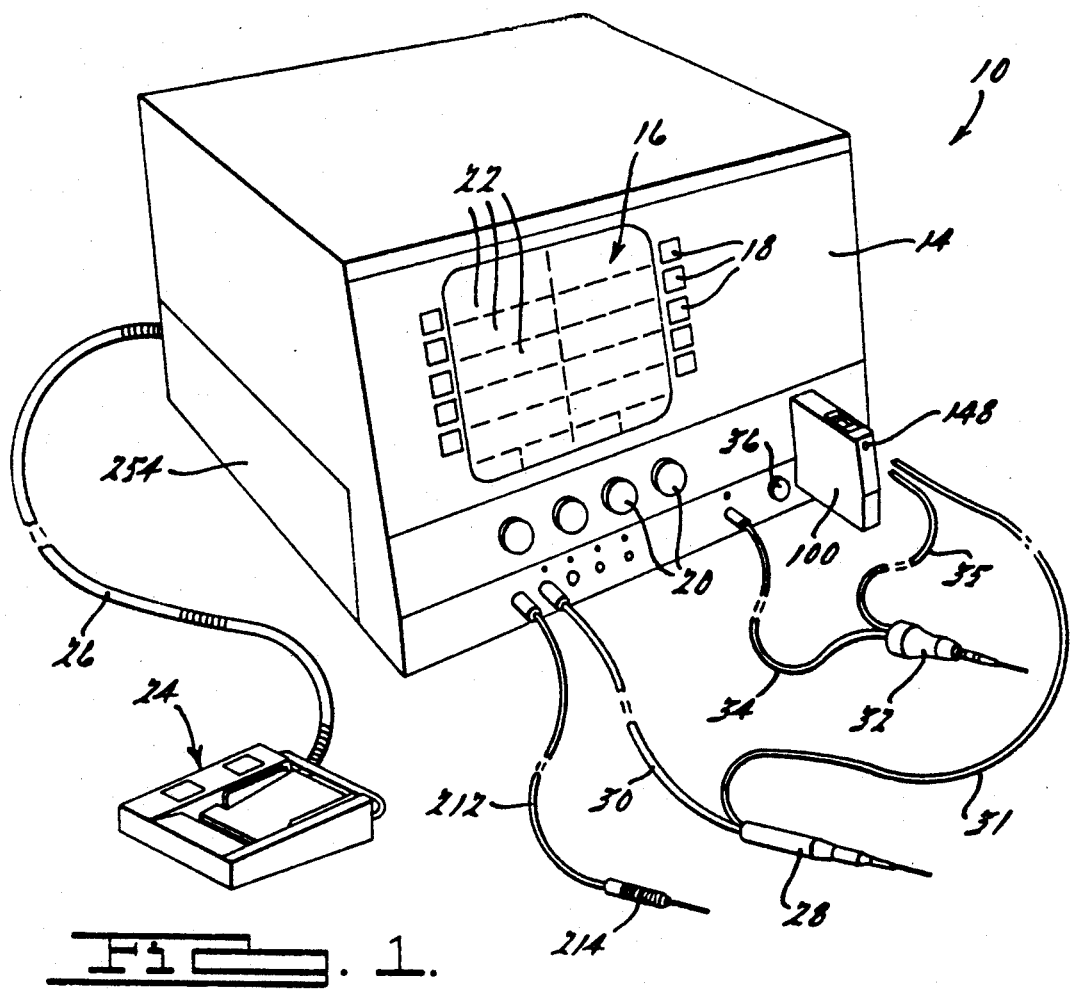
FIG. 1 is a perspective view of the microsurgical system of the invention.
Figure 2:
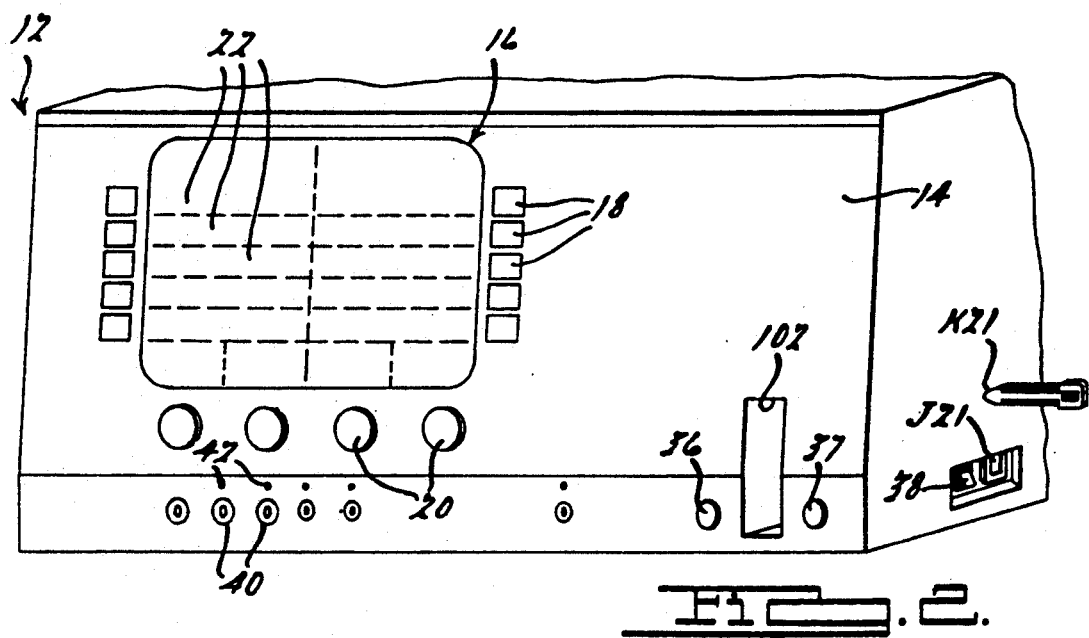
FIG. 2 is a front view of the system console showing the front panel layout in greater detail.

Referring first to FIGS. 1 and 2, a microsurgical control system 10 is provided having a foot pedal assembly 24 according to the present invention. The control system 10 includes a system console 12 which has an upwardly and inwardly sloping front panel 14 and at least one removable access door 254 in one of the side panels. On the front panel 14 is an electronic display screen 16, a plurality of push button switches or touch sensitive pads 18 and a plurality of "endless" digital potentiometer knobs 20. The push buttons 18 and knobs 20 are actuable by the surgeon or nurse to select various different modes of operations and functions used in various surgical procedures.

The console 12 also includes a cassette eject button 36, an irrigation pinch valve 37, and a power on/off switch 38.

The electronic display screen 16 is controlled by a computer to provide one or more different menus or messages which instruct the operator as to the function of the buttons 18 and knobs 20 for the particular mode selected. The display screen 16 may be conceptually divided into display screen regions 22 with the buttons 18 and knobs 20 being positioned at locations around the periphery of the screen 16 corresponding to the regions 22. By virtue of the location of the buttons 18 and knobs 20 adjacent the screen 16, for example, a message in the upper left-hand corner of the screen 16 is readily understood by the operator as referring to the upper left most button. This arrangement allows the indicated function of each button 18 and knob 20 to be readily changed. The use of an electronic display screen 16 also permits the buttons 18 and knobs 20 to be labeled in virtually any language.

The microsurgical control system 10 is adapted for use with a number of different surgical instruments. As shown in FIG. 1, a fiber optic illumination instrument 214 is coupled to the console 12 via fiber optic cable 212. Also illustrated is a fragmentation emulsification instrument 28 coupled to the console 12 through an electrical cable 30. The instrument 28 is also coupled to a collection container or cassette 100 through an aspiration tube 31. A cutting instrument 32 is also shown which is coupled to the console 12 through tubing 34 and to the cassette 100 through tubing 35. The cutting instrument 32 may be a guillotine cutter for vitrectomy procedures, or it may be a microscissors instrument for proportionate and multiple cutting. However, when the microscissors instrument is used, the instrument is not connected to the cassette 100.

While certain microsurgical instruments have been illustrated in FIG. 1, it will be understood that the microsurgical control system 10 can be used with other similarly equipped instruments. In general, any of the microsurgical instruments are actuated or controlled by fluid pressure (positive pressure or negative pressure). However, it should be appreciated that other suitable types of control signals may be used in the appropriate application.

To provide irrigation/aspiration capabilities, the control system 10 further includes the removable cassette 100 which may be inserted into a cassette slot 102 in the console 12. The cassette 100 has a passageway opening 148 to which an aspiration tube from an aspiration instrument may be connected. The console 12 also includes a plurality of couplers 40 to which surgical instruments described above may be attached. Above each coupler 40 is a light emitting diode 42 which is illuminated when the instrument connected to the associated coupler 40 is activated. To store the operating parameters of a particular microsurgical operation, the control system 10 electrically communicates with a digitally encoded memory key K21. The memory key K21 includes an integrated memory circuit which stores the operating parameters for a particular surgical procedure. The console 12 receives the key K21 through a slot J21. Suitable types of memory keys K21 are commercially manufactured by Data Key Inc., Burnsville, MN. However, it should be appreciated that other suitable means for accessing specifically assigned memory locations may be used in the appropriate application.

A further description of the control system may also be found in the following commonly owned patent applications which were filed on even date herewith, and which are hereby incorporated by reference: Scheller, et al U.S. patent application Ser. No. 928,265 filed Nov. 6, 1986, now U.S. Pat. No. 4,773,897 issued Sep. 27, 1988, entitled "Collection Container For Ophthalmic Surgical Instruments"; Scheller, et al U.S. patent application Ser. No. 927,827 filed Nov. 6, 1986, nnow U.S. Pat. No. 4,757,426 issued Jul. 12, 1988, entitled "Illumination System For Fiber Optic Lighting Instruments"; and Scheller U.S. patent application Ser. No. 927,807 filed Nov. 6, 1986, now U.S. Pat. No. 4,837,857 issued Jun. 3, 1989, entitled "Foot Pedal Assembly For Ophthalmic Surgical Instrument".

Figure 3:
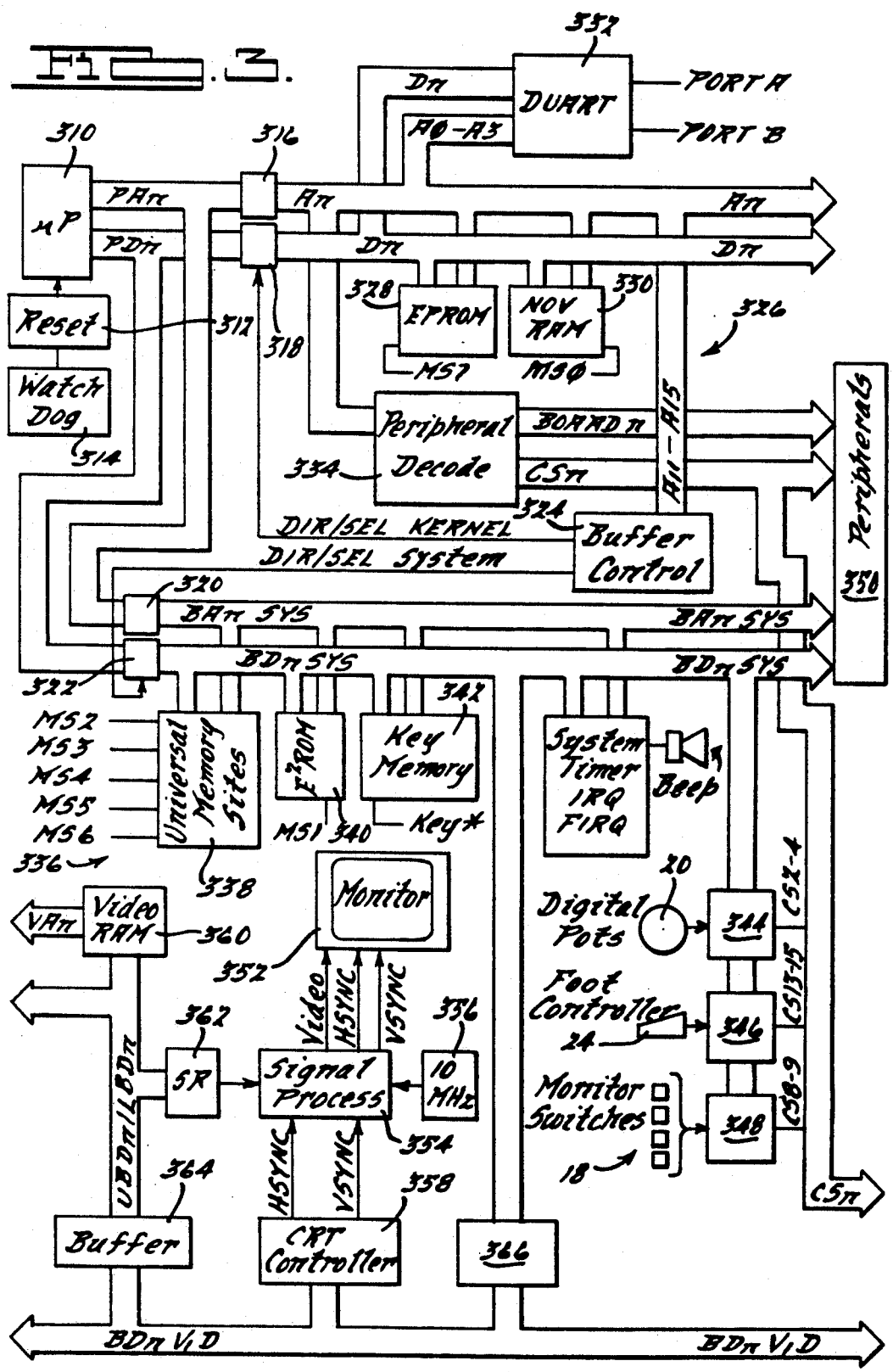
FIG. 3 is a system block diagram of the electronic control system of the invention.

Referring now to FIG. 3, a system overview of the microsurgical control system will be presented. The control system of the presently preferred embodiment centers around a microprocessor 310, such as a Motorola 6809. Connected to the reset terminal of the microprocessor is a reset logic circuit 312 and watchdog circuit 314. Reset logic circuit 313 performs the power on reset and manual reset functions, while the watchdog circuit monitors the operation of the microprocessor and causes it to be reset in the event it should enter an endless software loop or wait state. The details of the reset logic and watchdog circuits will be discussed below in connection with FIG. 5.

Microprocessor 310 communicates with a processor address bus PAn and with a processor data bus PDn. In the presently preferred embodiment, the address and data bus structure is divided into two parts, one part for addressing the kernel of the machine and the other part for addressing the higher level system components. The kernel provides most of the peripheral device-independent functions and gives the control system its default or start up characteristics. The higher level system portion gives the control system the capability of being programmed to handle a variety of different surgical procedures with response characteristics tailor fit to a particular surgeon. As seen in FIG. 3, the processor address bus PAn and the processor data bus PDn both branch forming two portions. The resulting four branches are buffered in buffers 316, 318, 320 and 322. Buffers 316 and 318 address the kernel of the machine on address bus An and data bus Dn. Buffers 320 and 322 address the system portion of the machine on address bus BAnSYS and on data bus BDnSYS.

In order to select whether the kernel portion or the system portion is to be addressed by microprocessor 310 and in order to maintain control over the direction of data flow, a buffer control circuit 324 is provided. Buffer control circuit 324 is responsive to address lines A11-A15 of address bus An. It provides a plurality of control signals coupled to buffers 318 and 322 for selecting which of the two data buses (Dn or BDnSYS) are active and for controlling the direction of data flow. Thus by addressing buffer control circuit 324, microprocessor 310 can selectively address either the kernel portion or the system portion of the invention.

The bulk of the kernel appears generally at 326 and includes EPROM 328 and nonvolatile RAM 330. EPROM 328 contains the kernel operating system program instructions while nonvolatile RAM 330 contains the default data values used to define the system's default operating parameters. Also coupled to the kernel is dual UART (DUART) 332 which provides serial communication with microprocessor 310 via ports A and B. These ports may be accessed in order to monitor the microprocessor machine states during software debugging and programming and may also be used to connect to an external computer system for use in loading updated software into the machine and for testing the system. If desired, either or both of the ports can be connected to modem circuits for remote communication with the system via telephone lines. This feature would permit software updates to be made without requiring the unit to be shipped back to the factory.

Also part of the kernel 326 is a peripheral decoding circuit 334 which is coupled to address bus An and which provides a plurality of board select signals BOARDn and a plurality of chip select signals CSn, which microprocessor 310 can activate to select a particular peripheral controller board or to select a particular peripheral controller chip. These will be discussed more fully below.

The system portion of the invention is illustrated generally at 336. The system portion communicates with the system buses BAnSYS and BDnSYS. Included in the system portion are a plurality of universal memory sites 338 which can contain random access memory chips programmed to contain alternate response characteristics which differ from the default characteristics stored in RAM 330. Also provided is EEROM 340 which is an electrically erasable ROM used to store the calibration arrays for determining the response of the pneumatic systems or fluid pressure controlled systems of the invention. The values stored in EEROM 340 represent calibration values preferably set and stored at the factory. Because an electrically erasable ROM is used, these values can be erased and updated under appropriate software control. In the presently preferred embodiment, this reprogramming is not available to the end user, but would normally be performed by a qualified technician via the serial ports A and B of dual UART 332. The microfiche appendix provides one example of a suitable program which could used in the control console according to the present invention. This microfiche appendix is hereby incorporated by reference.

Each of the universal memory sites 338, as well as EEROM 340, EPROM 328 and nonvolatile RAM 330 include a memory select control input MSn. Control circuit 324, under microprocessor control, provides the memory select signals used to activate a particular memory device. In addition to these memory devices, the invention also has the capability to address a removable memory device which can be removably connected to a jack accessible on the exterior of the system console. This removable memory device or key memory 342 may be programmed by the end user for storing parameters used to define particular surgical procedures and particular response characteristics desired by a given surgeon. Although the key memory devices may be implemented in a variety of different package configurations, the presently preferred configuration is in the form of a removable electronic key. The key has a plurality of electrical contacts connected to a nonvolatile electrically alterable memory chip which is encapsulated in the body of the key. When the key is inserted into the jack on the system console and turned, the encapsulated memory chip is coupled to the key memory space 342 of the system portion of the circuit. The particular parameters and surgical procedures stored in the key memory are then accessible to microprocessor 310 to override the default parameters stored in nonvolatile RAM 330. It should be noted, however, that the key is only necessary to override the default values, and that the system may be operated without the key using the default values.

In order to provide an interface between the human operator and the control system, several human actuable controllers are provided. These controllers include a plurality of "endless" digital potentiometers 20 and associated buffering circuitry 344 to which the front panel potentiometer knobs 20 are connected. In one embodiment according to the present invention, these digital potentiometers are Hewlett Packard Model HEDS7501 controllers. The signals generated by these potentiometers are related to specific operating parameters by the software. Accordingly, it should be that this feature permits multiple uses to be made of these potentiometers for different surgical procedures. As will be seen in connection with FIGS. 18-31, the display screen 16 is used to display an indication of the special operating parameters for these potentiometers.

The digital potentiometers are connected to the system data bus BDnSYS and are selected by activation of certain of the chip select lines (CS2-CS4). The foot controller pedal 24 coupled to foot control circuitry 346 also provides human actuable control via the system data bus. In addition, push buttons 18 likewise provide human actuable control. These buttons are coupled through push button interface circuitry 348 to the system data bus. Like the digital potentiometer circuitry, the foot control circuitry and the push button interface circuitry are selected by certain of the chip select lines. The foot controller is selected by chip select lines CS13-CS15, and the push button circuits are selected by CS8-CS9.

The human actuable controllers, i.e. the digital potentiometers, the foot controller pedal and the push button monitor switches, may be considered as peripheral devices. In addition to these peripheral devices, the microsurgical control system 10 also includes several analog peripheral devices, i.e. the fluid pressure actuated surgical implements. To simplify the illustration in FIG. 3, these analog peripherals and their associated control circuitry have been designated generally by block 350.

The microsurgical control system also includes a video monitor 352 which defines display screen 16 and on which human readable messages are displayed. As will be more fully explained below, monitor 352 displays a series of different menus which identify the current function of each of the monitor switches 18 and digital potentiometers 20. In addition, the menus also provide certain other information to the surgeon, such as the operating parameter values selected by the appropriate rotation of the digital potentiometers. The video monitor is supplied with horizontal and vertical sync signals and a video signal via signal processor circuit 354. Signal processor circuit 354 receives the 10 MHz clock signal from oscillator 356 as well as the vertical and horizontal sync signals from CRT controller 358. Each of the pixel locations on monitor 352 has one or more corresponding memory cell locations within video RAM circuit 360. The video RAM circuit is a dual ported memory circuit which can be directly accessed by both the monitor via the shift register (SR) interface circuit 362 and which may be accessed by the microprocessor via buffer 364. The presently preferred video screen has a 256 by 512 pixel resolution. Data to be displayed on monitor 352 is input through buffer 364 to video RAM 360 during a first half of the microprocessor machine cycle. During the second half of the machine cycle, the data is converted to a video signal and written to the monitor for display. As illustrated in FIG. 3, the monitor circuit defines a separate buffer data bus BDnVID, which is coupled to the system data bus BDnSYS through buffer 366.

Because many of the peripheral devices are interrupt handled devices, a system timer and interrupt request circuit 368 is provided. When a peripheral device needs attention of the microprocessor, it generates an interrupt which is handled by the interrupt request circuit 368, causing the appropriate microprocessor interrupt to be generated. Circuit 368 also generates a system timer which is coupled to a speaker 370 to produce a periodic audible beeping tone. The audible beeping tone is presently tied to the aspiration function. It provides a tone which periodically beeps at a rate proportional to the aspiration rate. The audible beeping tone provides a continuous audible indication of the aspiration rate so that the surgeon does not need to look away from the surgical situs in order to determine the aspiration level.

Having given an overview of the microsurgical control system, a more detailed analysis of the circuit will now be presented.

The detailed schematic diagrams of FIGS. 4-17 have been provided with the customary pin designations where applicable. In these detailed schematic diagrams, many of the interconnecting leads and buses have been omitted for clarity; and it will be understood that the circuits with like pin designations share common signal lines and buses.

Figure 4:
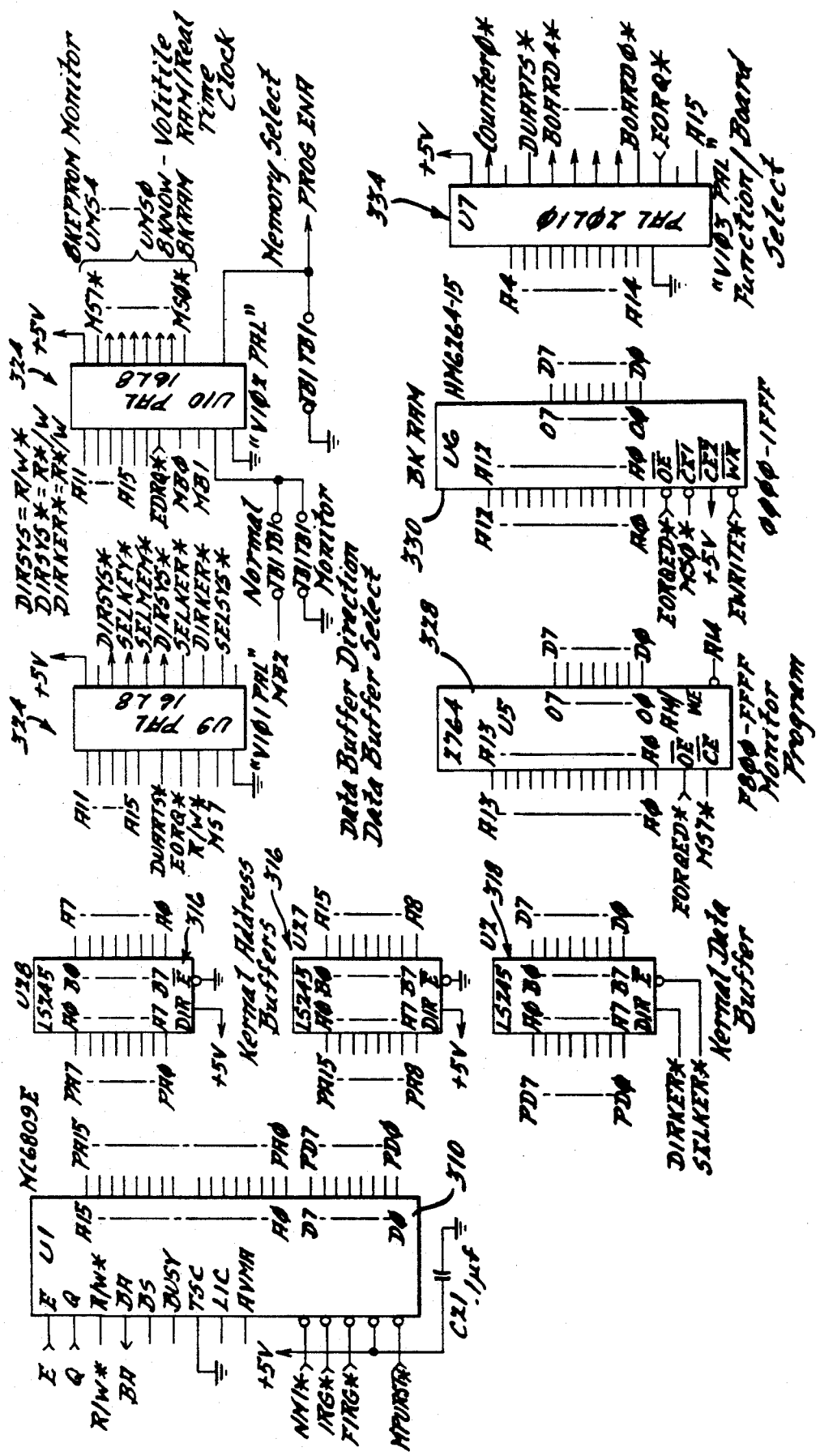
FIG. 4 is a detailed schematic diagram illustrating the processor and related components of the electronic control system.

Referring now to FIG. 4, microprocessor 310 is illustrated. In FIG. 4, microprocessor 310 is also designated U1. The kernel address buffer 316 comprises two buffer circuits U27 and U28 which may be LS245 integrated circuits. The kernel data buffer 318 is implemented using buffer circuit U2 which may also be a LS245 integrated circuit. The DIR terminal of circuit U2 is responsive to the DIRKER* control signal and the E* terminal is responsive to the SELKER* control signal. The SELKER* control signal selects the kernel data bus as the active bus and the DIRKER* control signal controls the data flow direction. These control signals are generated by the buffer control circuit 324 which includes circuits U9 and U10, both programmable array logic chips, such as PAL16L8 integrated circuits. These circuits are coupled to the A11-A15 address lines and decode these lines to produce the control signals indicated in FIG. 4. Among the control signals provided are memory select signals MSN (MS0-MS7). These signals are used to select which of the memory chips is being accessed by microprocessor 310.

Also illustrated in FIG. 4 is EPROM 328 and nonvolatile RAM 330. These memory circuits are also designated U5 and U6, respectively. EPROM 328 may be a 2764 integrated circuit, while nonvolatile RAM 330 may be an HM6264-15 integrated circuit. As illustrated, EPROM 328 is enabled by MS7 memory select signal while RAM 330 is enabled by the MS0 memory select signal.

Also illustrated in FIG. 4 is peripheral decode circuit 334, which is also designated U7. This circuit may be a PAL20L10 integrated circuit. It provides the function selection and board selection by decoding address lines A4-A15. In addition to providing the BOARDn control signals (BOARD0-BOARD1), U7 also provides several other control signals indicated, including a control signal for operating dual UART 332. In addition to circuit U7, the peripheral decode circuit 334 also comprises circuit U8, shown in FIG. 6. Circuit U8 may be an LS154 integrated circuit which decodes address lines A0-A3 and provides a plurality of chip select signals CSn (CS0-CS15). As illustrated, circuit U8 is enabled by the BOARD0* signal from U7.

Figure 5:
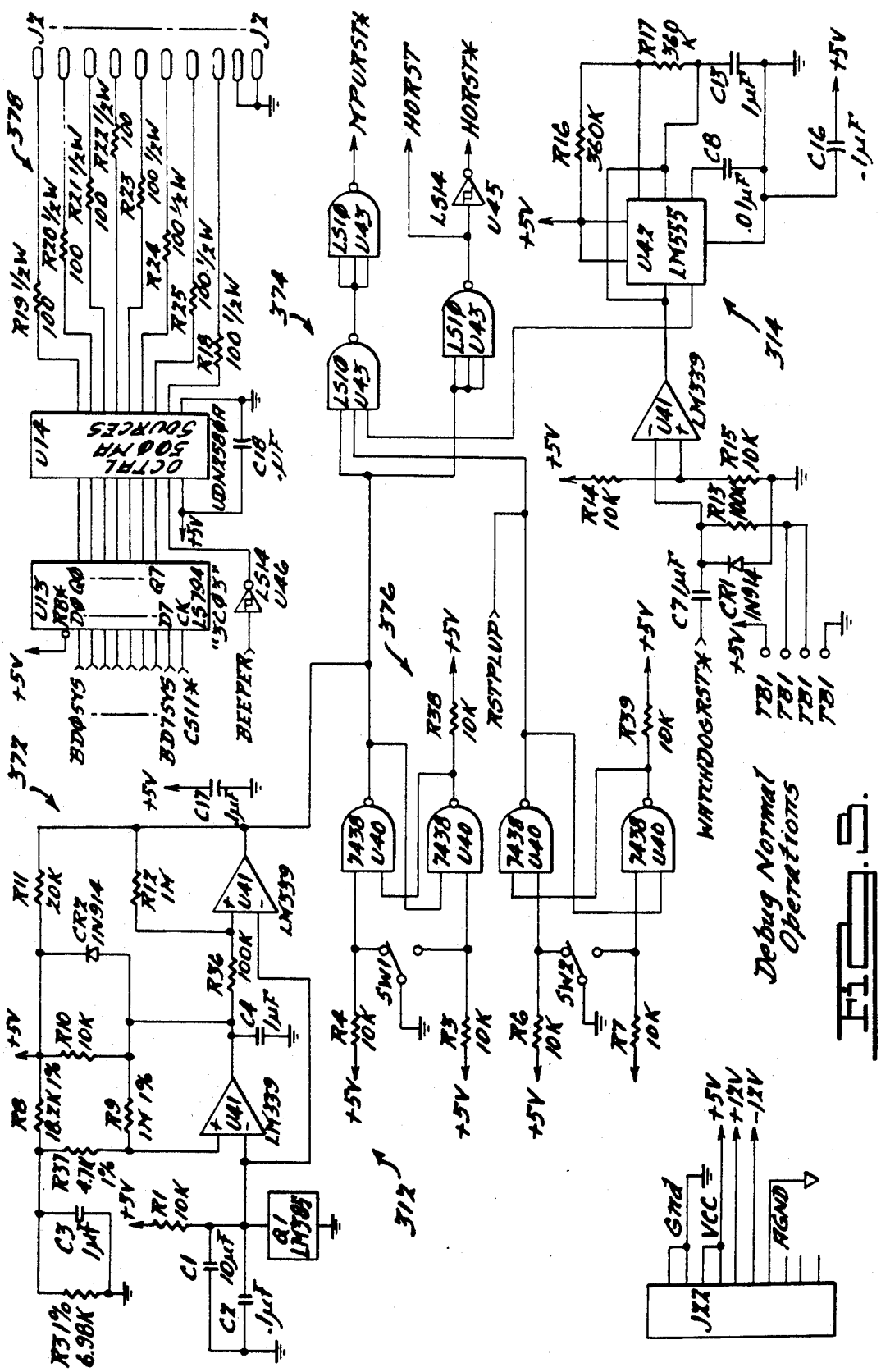
FIG. 5 is a detailed schematic diagram illustrating the reset and watchdog circuits of the electronic control system.

Referring now to FIG. 5, the reset logic circuits 312 and watchdog circuit 314 are illustrated. The reset logic circuits provide an output at circuit U43 which is designated MPURST*. This signal is coupled to microprocessor 310 (FIG. 4) to provide a reset signal to the microprocessor. The reset circuits include a power on reset circuit 372 which couples to the reset logic circuit 374. The power on reset circuit provides a reset signal a sufficient time after powerup to ensure that the microprocessor is properly operating. Reset logic circuit 374, in addition to providing the microprocessor reset signal MPURST*, also provides hardware reset signals HDRST and HDRST* for resetting the peripheral devices connected to the system. This arrangement allows the microprocessor to be reset, to change memory banks for effecting different operations, for example, without requiring the hardware reset of the peripheral devices. The reset functions may be instigated by software control or by manually operated reset push buttons. The reset logic circuits 312 include a reset button control logic circuit 376 through which manual reset of both the microprocessor and the system can be accomplished using switches SW1 and SW2.

Watchdog timer circuit 314 is a resettable timer circuit. During normal operation, the microprocessor, acting through control signal WATCHDOGRST*, resets or reinitializes the watchdog circuit every 40 to 50 milliseconds. The watchdog reset control signal WATCHDOGRST* is provided by the dual UART 332, shown in FIG. 7. As long as the watchdog circuit is periodically reinitialized, it will not affect operation of the microprocessor. However, if not reinitialized after approximately 200 to 300 milliseconds, watchdog circuit 314 produces an output signal which causes the microprocessor reset signal MPURST* to be generated.

One purpose of the watchdog circuit is to reset the microprocessor and the system in the event the microprocessor loses program control due to a power surge or dropout. This is implemented by requiring the microprocessor to periodically generate the watchdog reset control signal as one of its many functions. If program control is lost, the microprocessor will not generate this control signal, whereupon the watchdog circuit 314 will cause a reset.

Another use for the watchdog circuit is in switching between memory banks. The control system of the invention employs several memory banks, which are discussed more fully below. These memory banks may be programmed to contain different sets of instructions, operating parameters, and the like. Normally, the microprocessor would operate based on instructions contained in one or more of the memory banks, with the remaining banks containing different instructions held in reserve for other users. For example, the memory banks may be programmed to display operating instructions in a variety of different languages: English, French, German, Japanese and so forth. In order to switch from one bank to another, the microprocessor executes program instruction code which appropriately changes the default memory to be selected. The microprocessor then purposefully fails to reinitialize the watchdog circuit, causing a reset to occur. When the reset occurs, the machine state reinitializes with the newly selected memory bank in place of the previously selected one. Also, if desired, hardware switches or jumpers may be used to determine which memory banks are active upon power up.

Also illustrated in FIG. 5, is the indicator driver circuitry 378 which is used to illuminate the LED indicators 42 above the couplers 40 on the front panel of console 12.

Figure 6:
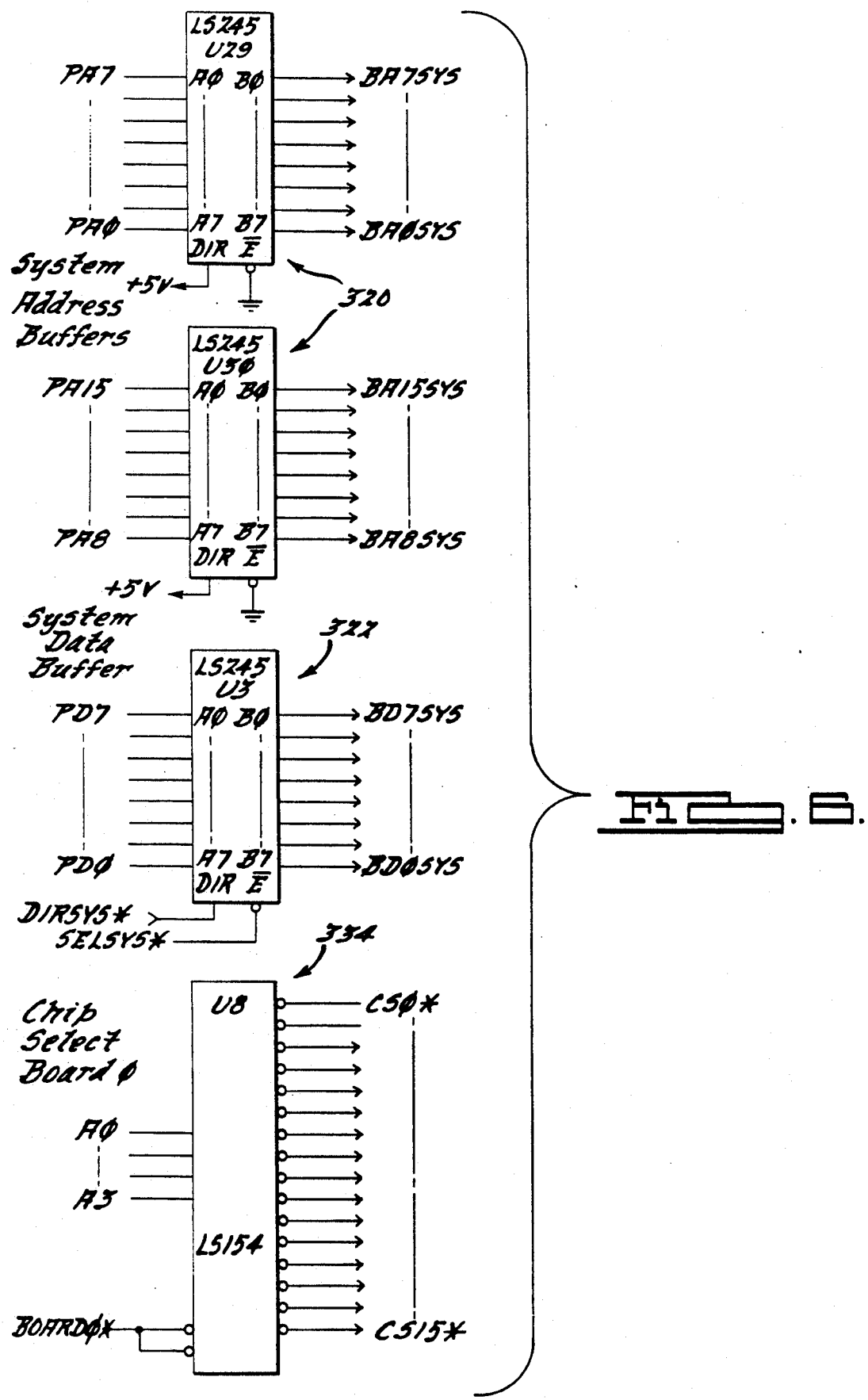
FIG. 6 is a detailed schematic diagram illustrating the system bus structure of the electronic control system.

Referring now to FIG. 6, the system address buffers 320 and system data buffer 322 are illustrated. System address buffers 320 are designated U29 and U30 while system data buffer is designated U3. Like the kernel data buffer 318, the system data buffer 322 has its DIR and E* terminals connected to control lines DIRSYS* and SELSYS* which are provided by buffer control circuit 324.

Figure 7:
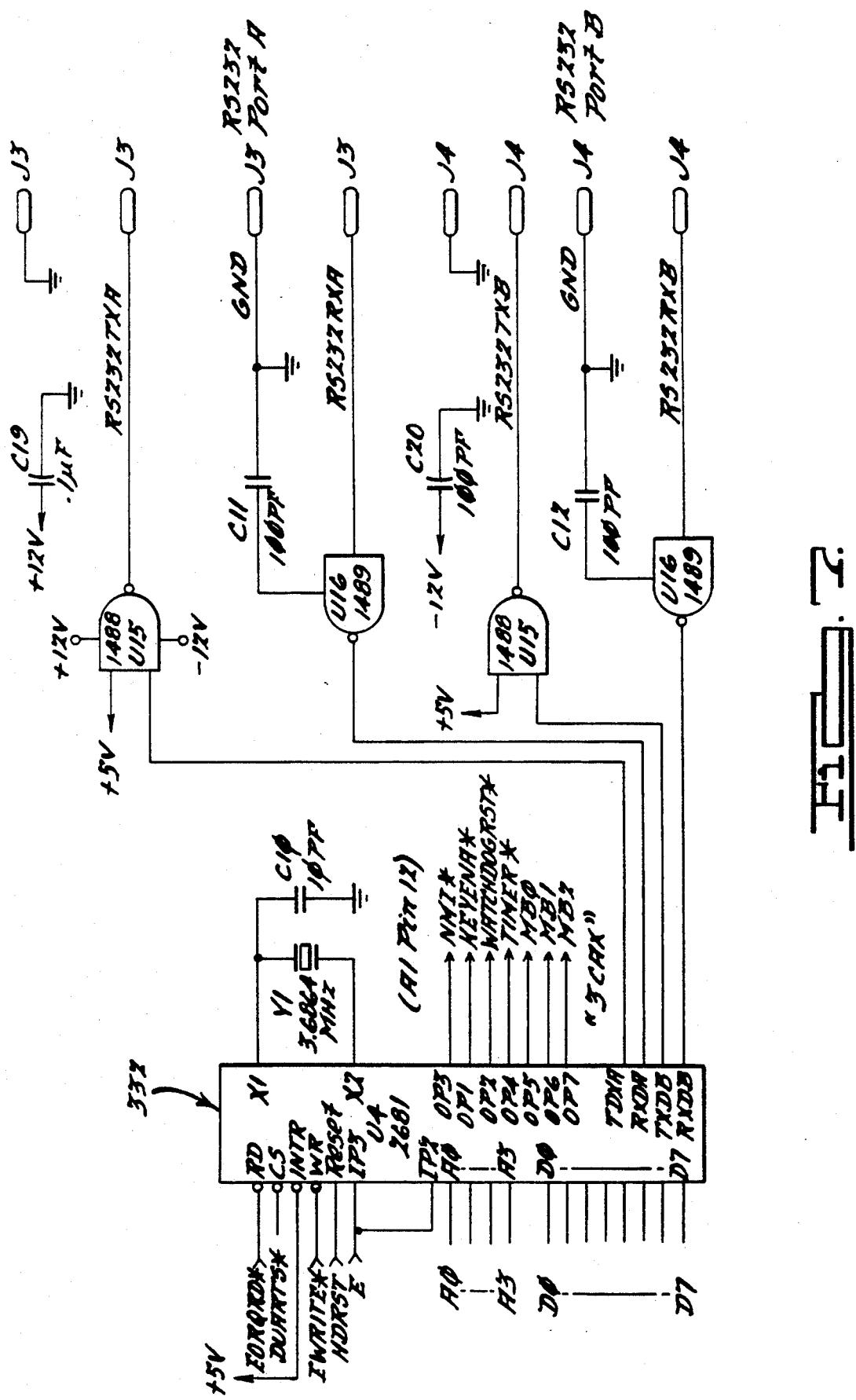
FIG. 7 is a detailed schematic diagram illustrating the dual UART circuit of the electronic control system.

FIG. 7 illustrates the dual UART circuitry 332 in greater detail. As illustrated, the dual UART circuitry includes a dual UART chip U4 which may be a 2681 integrated circuit. This circuit provides the various control signals indicated, including the watchdog reset control signal previously discussed. The dual UART circuit 332 provides two ports Port A and Port B, both complying with the RS232 standard. Although the uses of these two ports are many, one use is in loading new programs into the memory of the system. One of the ports can be connected to a remote terminal to receive commands, while the other terminal can be used to input the program to be loaded. In this fashion, the state of the machine can be monitored during the program loading procedure.

Figure 8:
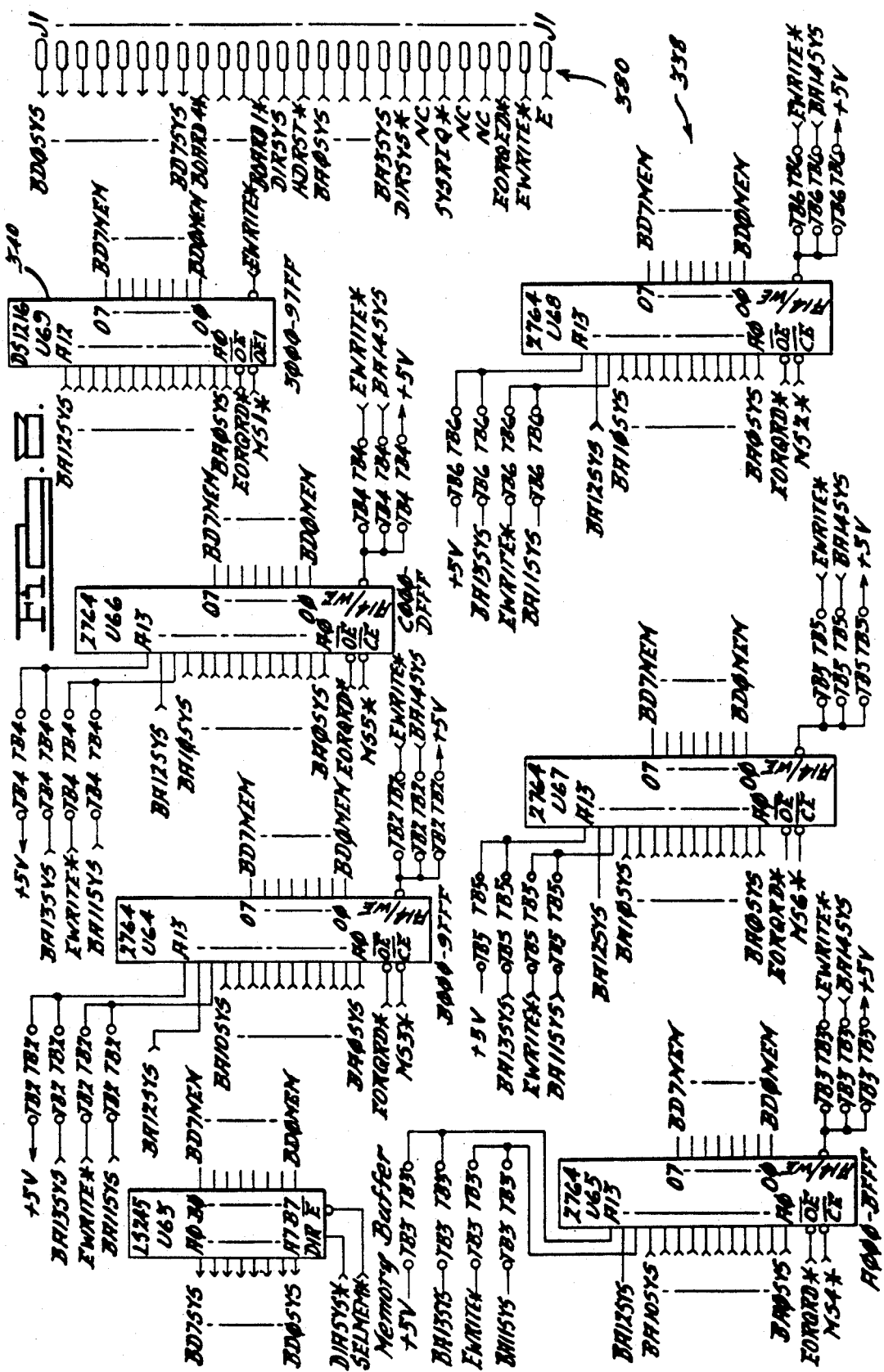
FIG. 8 is a detailed schematic diagram illustrating the memory circuits of the electronic control system.

FIG. 8 depicts the universal memory sites 338 of the invention. These universal memory sites may be provided with either RAM or ROM, depending upon the desired application. The universal memory sites are presently illustrated as circuits U64–U68, which may be implemented using 2764 integrated circuits. As illustrated, each of these circuits is coupled to one of the memory select lines MSn (MS2–MS6). Also illustrated in FIG. 8 is EEROM ROM 340, also designated U69. This circuit may be implemented using a DS1216 electrically erasable ROM circuit. As illustrated, the EEROM 340 is coupled to the MS1 memory select line. Also illustrated for convenience is the system bus 380 to which the universal memory sites 338 and EEROM 340 are connected.

Figure 9:
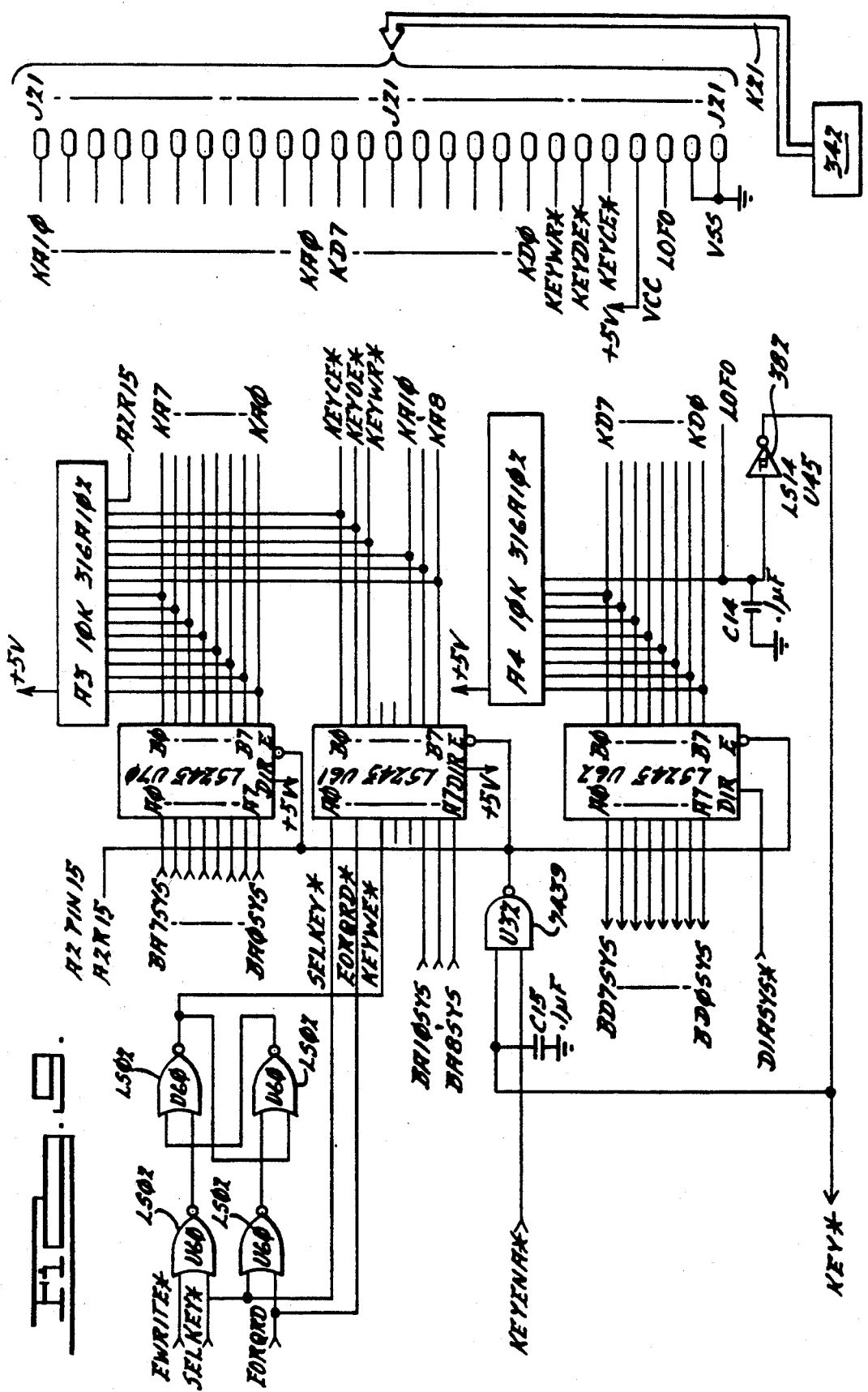
FIG. 9 is a detailed schematic diagram illustrating the key memory circuits of the electronic control system.

The key memory control circuitry is illustrated in FIG. 9. When the key K21 is inserted into jack J21, the key memory 342 is coupled to the KAn and KDn address and data buses. These buses are buffered through to the BAnSYS and BDnSYS system buses as illustrated. When the user physically turns the key in which the key memory 342 is encapsulated, a grounding signal is established with integrated circuit U32 (FIG. 12); and the KEY* signal enables the key memory 342 through Schmidt trigger 382.

Figure 10:
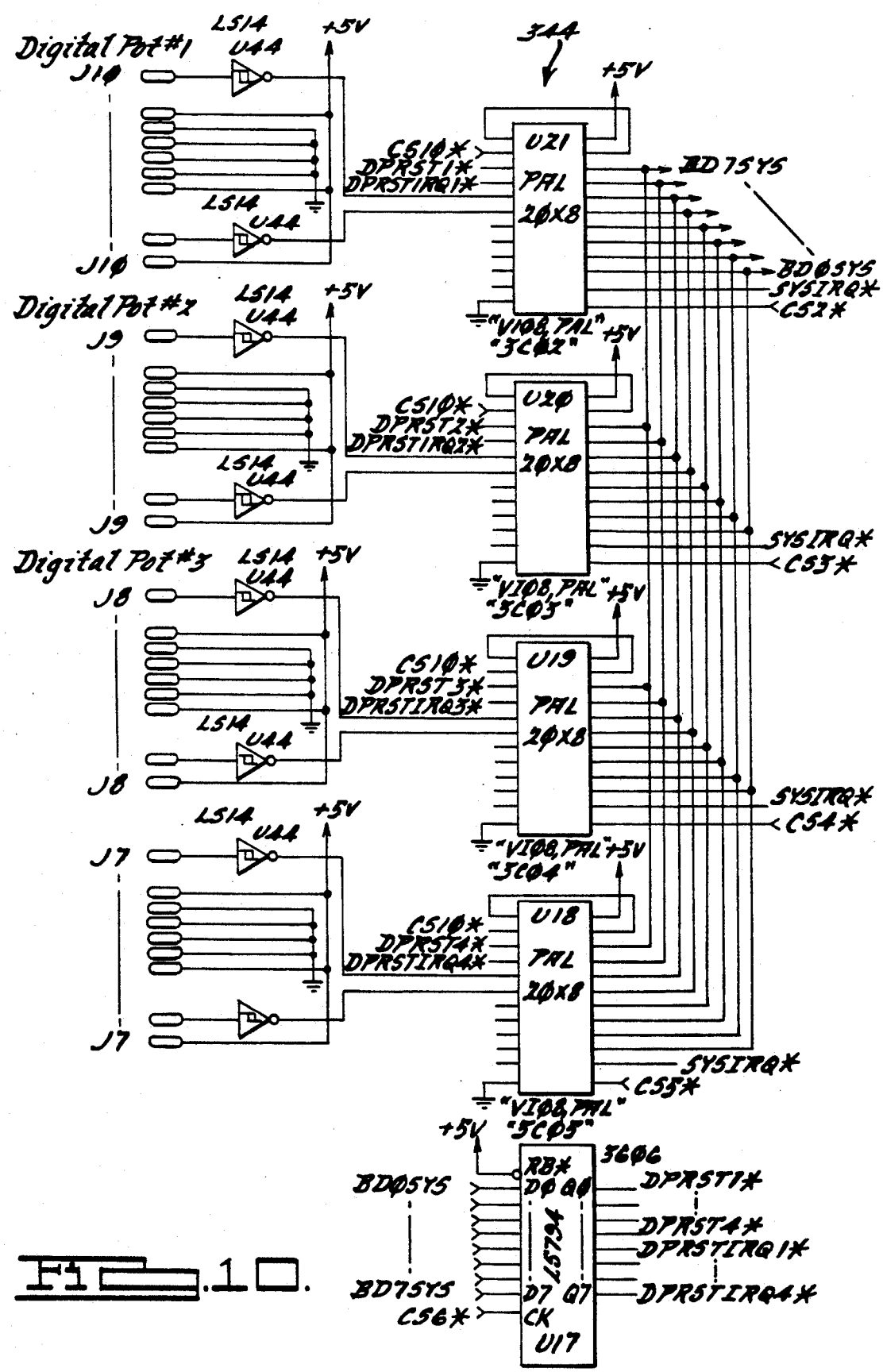
FIG. 10 is a detailed schematic diagram illustrating the digital potentiometer circuits of the electronic control system.

With reference to FIG. 10, the digital potentiometer control circuits 344 are illustrated in detail. Presently four digital potentiometers are illustrated, although it will be recognized that a greater or fewer number may also be employed. Each of the digital potentiometers is coupled to a programmable array logic (PAL) circuit, designated U18–U21. These PALS or logic array circuits are used to encode the signals from the potentiometers in order to provide an input signal which may be readily counted by counter circuitry which is internal to the microprocessor. Additionally, it should be noted that while these potentiometers may continue to be endlessly turned in one direction or the other, the counter will not go below a zero value or go above its maximum value. These logic array circuits are coupled to the system bus BDnSYS as illustrated. Each logic array is activated by a given chip select line CSn (CS2–CS5). Each logic array provides a system interrupt request signal on the lead designated SYSIRQ*.

When any one of the "endless" digital potentiometers is turned, the corresponding array logic circuit issues a system interrupt request which is handled by the interrupt request circuit 368 shown in FIG. 12. Preferably the value of each digital potentiometer is stored in a software variable and is updated each time the setting of the potentiometer is changed.

Figure 11:
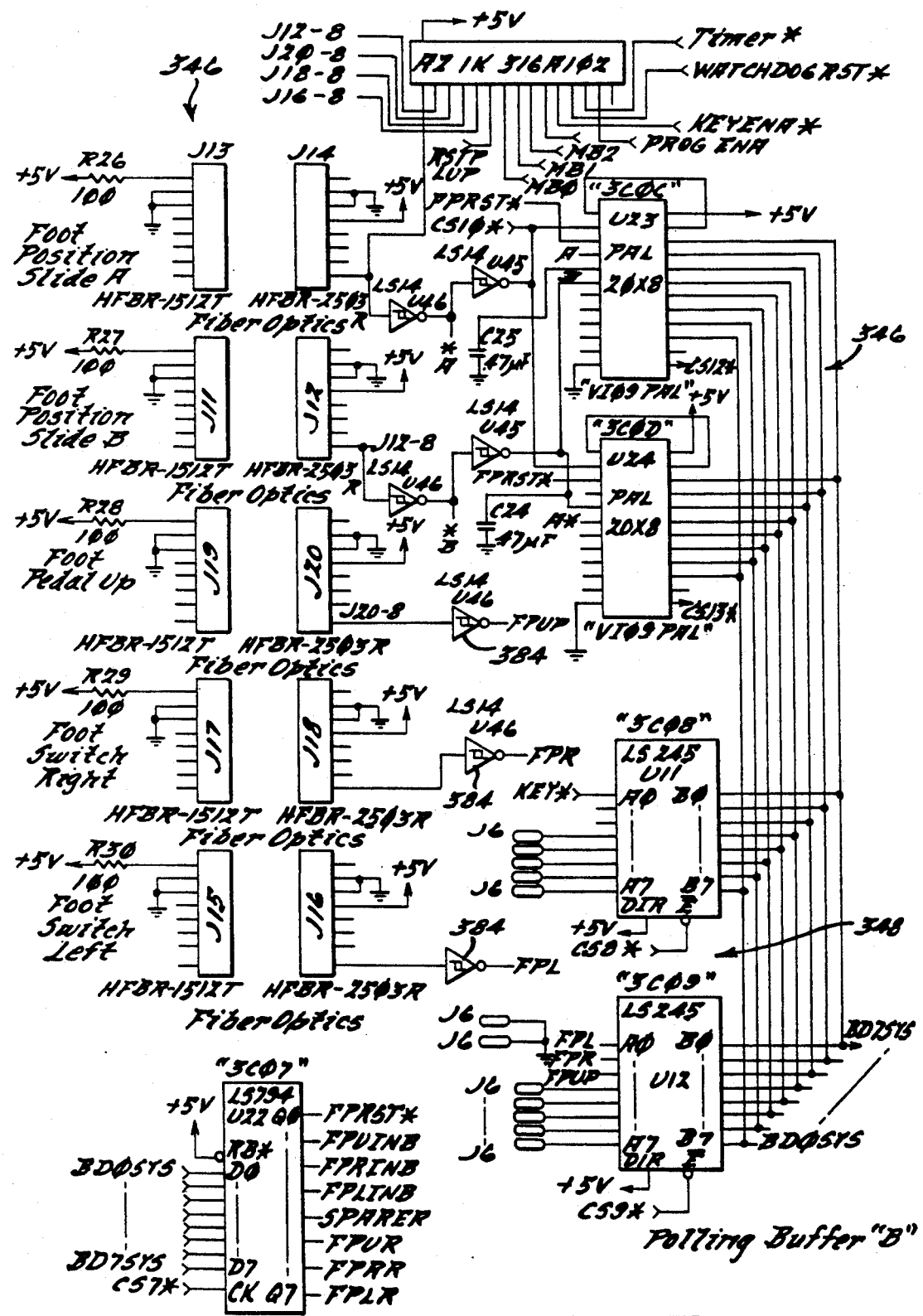
FIG. 11 is a detailed schematic diagram illustrating the foot controller pedal circuitry of the electronic control system.

FIG. 11 depicts the foot control pedal circuitry 346. The foot control pedal 24 is coupled by fiber optic cable 26 to the system console. A group of programmable array logic circuits designated U23, U24, U25 and U26 (FIG. 12) decode the foot pedal slide position settings indicative of the degree of rotation of the pedal about its generally horizontal axis of rotation. In addition to these values, the foot pedal also has an on/off switch which indicates that the foot pedal is in the fully up position. The foot pedal also has similar on/off switches which indicate when the foot switch has been moved to the right and left positions. These switches provide control signals via Schmitt triggers 384 designated FPUP, FPR and FPL.

FIG. 11 also illustrates the push button interface circuitry 348, comprising integrated circuits U11 and U12. The interface circuitry can be implemented using LS245 integrated circuits. The push buttons 18 (FIG. 1) are connected to jacks J6. Also connected to the interface circuitry 348 are the three control signals FPL, FPR and FPUP which are produced by the foot pedal switches discussed above. The circuits U11 and U12 couple all of the switches to the system bus BDnSYS.

The human actuable controllers are all transition detection interrupts peripheral devices. When the actuator setting is changed, a transition occurs which causes an interrupt signal to be generated. FIG. 12 illustrates the interrupt handling circuitry 368. The interrupt request handling circuit 368 includes integrated circuit U50 which may be an MC6840 integrated circuit. This circuit produces the system timer interrupt SYSFIRQ* which occurs every 40 to 50 milliseconds and is used for event counting and for resetting the watchdog circuit 314. This circuit also provides the audible beeping tone for driving speaker 370. Circuit 368 also includes logic gates 386 which are coupled to the foot pedal control signals FPUP, FPUR, FPR, FPRR, FPL and FPLR. The logic gates provide the system interrupt request signal SYSIRQ* which is coupled to U50 as shown.

Figure 13:
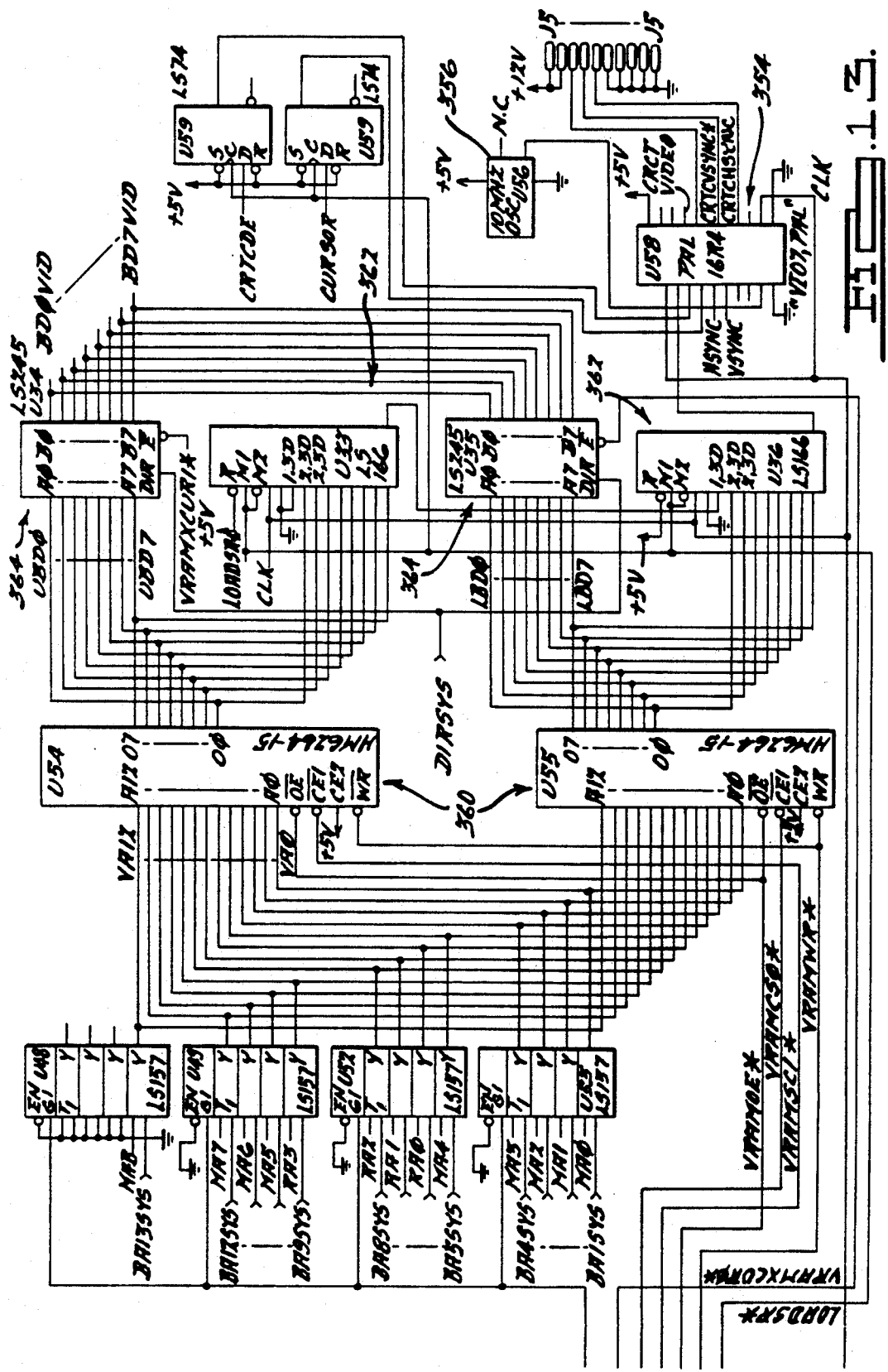
FIG. 13 is a detailed schematic diagram illustrating the video circuitry of the electronic control system.
Figure 14:
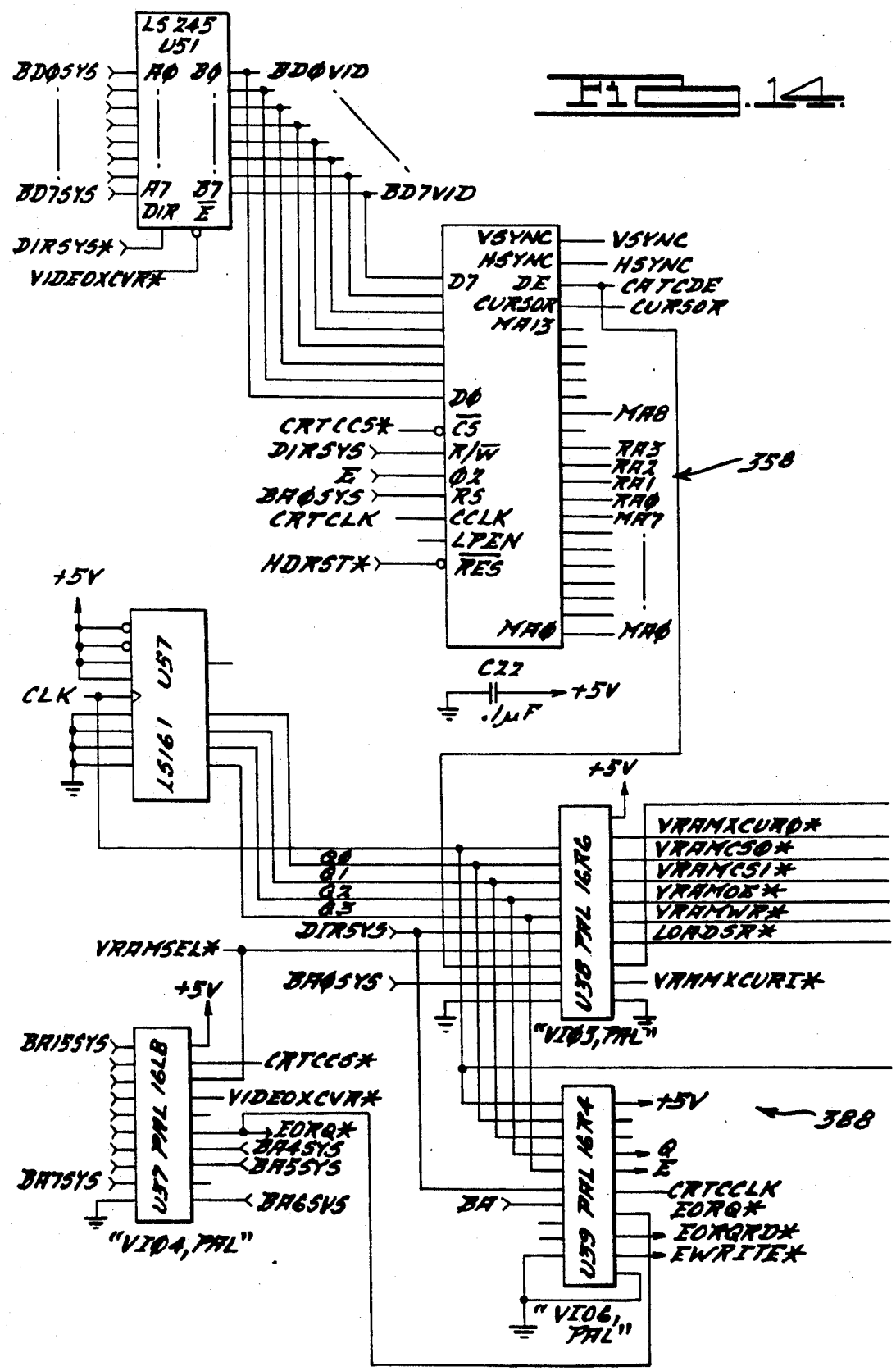
FIG. 14 is a detailed schematic diagram also illustrating the video circuitry of the electronic control system.

FIGS. 13 and 14 illustrate the video portion of the control system. The video circuitry includes CRT controller 358 which may be a 6845 integrated circuit. The CRT controller is illustrated in FIG. 14 bearing the designation U47. Coupled to the CRT controller is data bus buffer U51 which buffers the system data bus BDnSYS to the video data bus BDnVID. The CRT controller provides the vertical and horizontal sync signals VSYNC and HSYNC, as well as other control signals as indicated.

The video RAM memory circuits 360 are illustrated in FIG. 13. They are coupled to the video address bus VAn and also to the video data buses UBDn and LBDn. Buffers 364 comprising circuits U34 and U35 provide the buffering between these data buses and the system video data bus BDnVID. Circuits U34 and U35 may be LS245 integrated circuits. The DIR terminal of those circuits are mutually coupled to the DIRSYS control line. In order to access video RAM 360, the microprocessor writes data to buffers 364 during a first half of the microprocessor machine cycle. This data is written to the display monitor screen during the second half of the machine cycle. A ten MHz oscillator 356 provides the timing signal at which the video screen is refreshed during each other half cycle. Data is read from video RAM 360 into shift register (SR) interface circuits 362. This data is then shifted out at the ten MHz. rate into video signal processor circuit 354. The shift register interface circuits may be LS166 integrated circuits and are designated as U33 and U36 in FIG. 13. The signal processor circuit 354 is designated U58 and may be implemented using a PAL16R4 integrated circuit.

The output of signal processor circuit 354 provides the video and corresponding horizontal and vertical sync signals for driving the video monitor 352. Video RAM 360 is addressed using multiplexers U48, U49, U52 and U53, which are all implemented using LS157 integrated circuits. These multiplexers are in turn controlled by the timing and decoding circuitry 388 shown in FIG. 14. Timing decoding circuit 388 includes U38 which provides decoding for the video signal and U39 which provides timing for the system.

Figure 15:
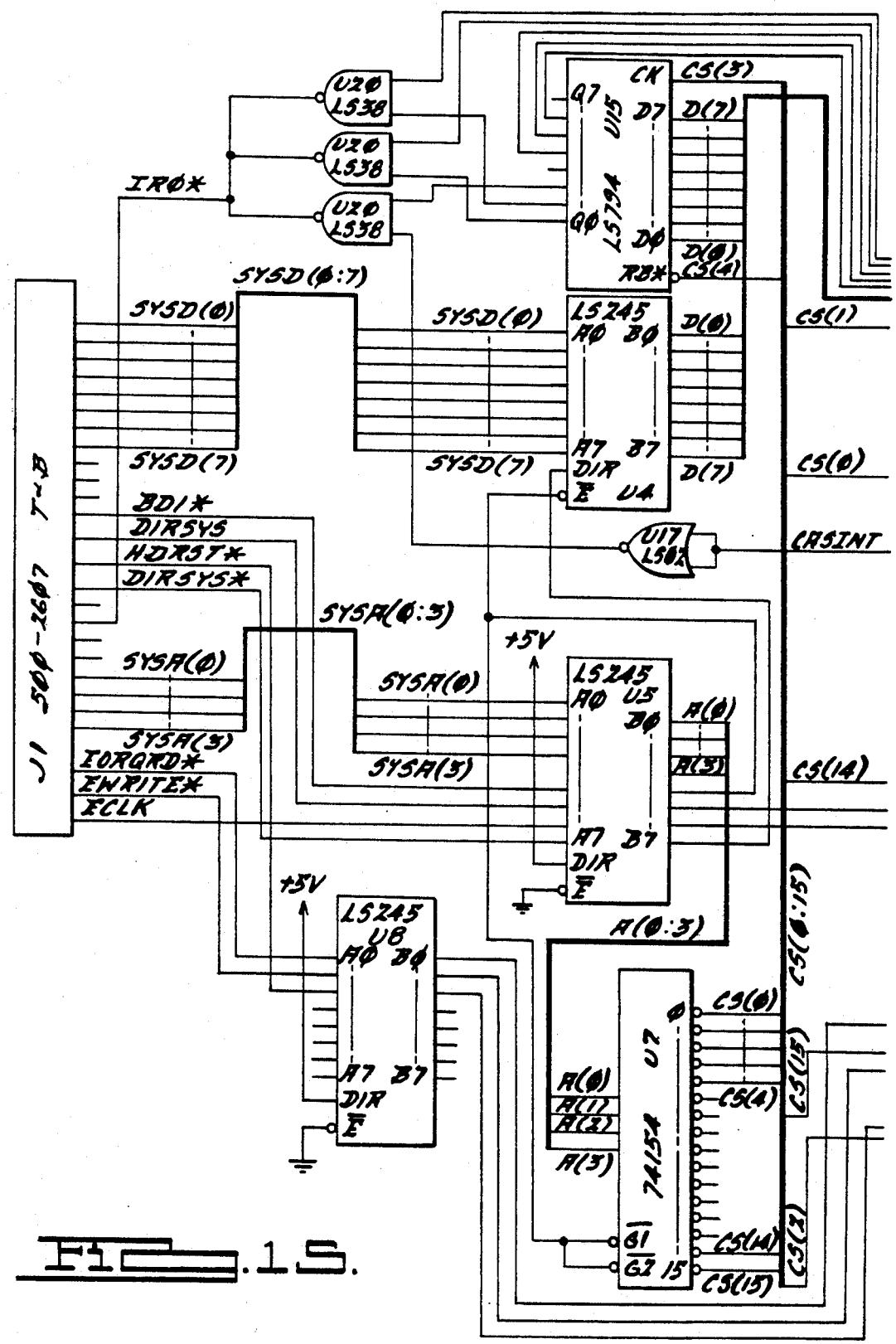
FIGS. 15-17 are detailed schematic diagrams illustrating the analog peripheral control circuitry of the electronic control system.
Figure 16:
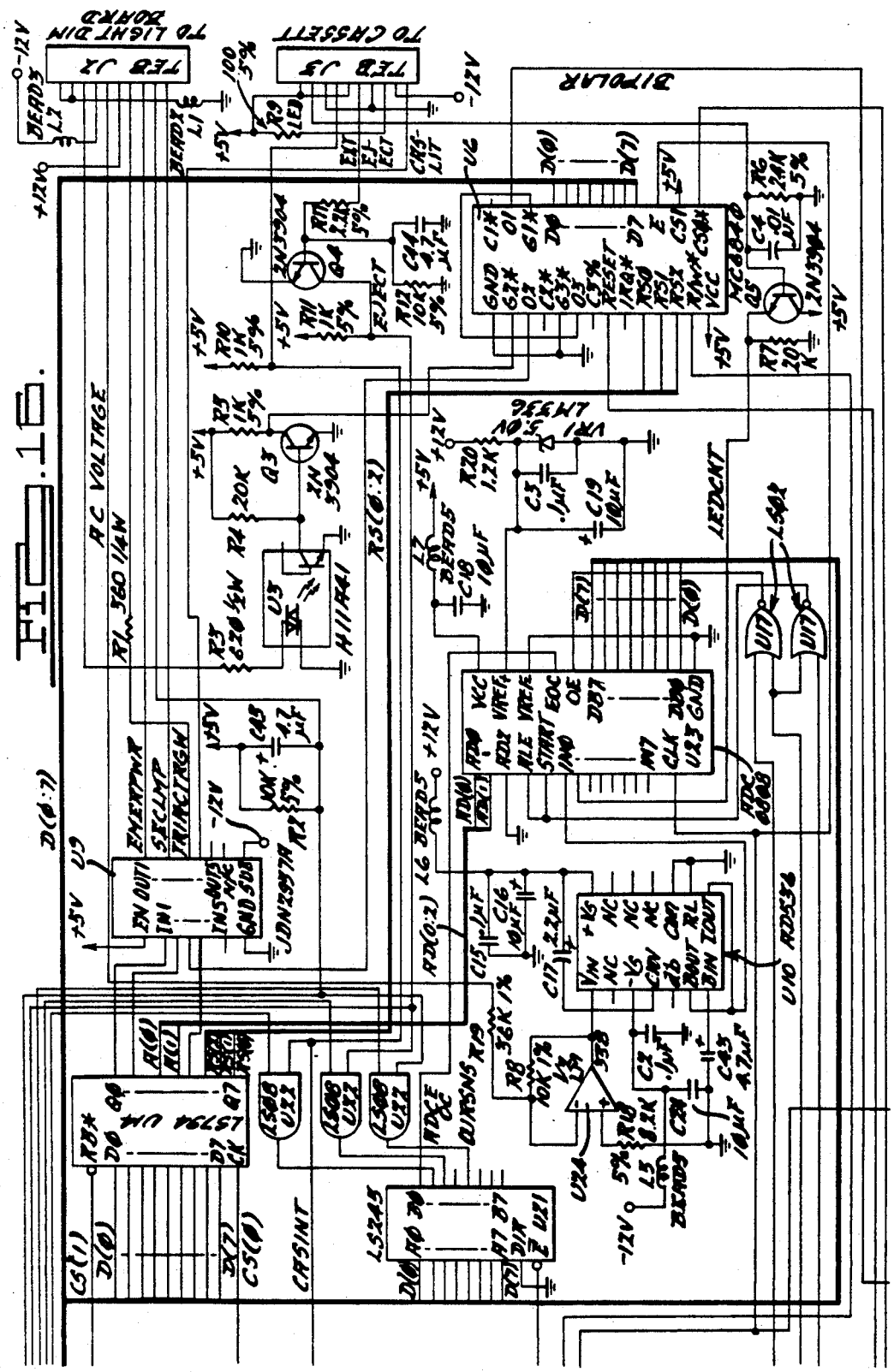
Figure 17:
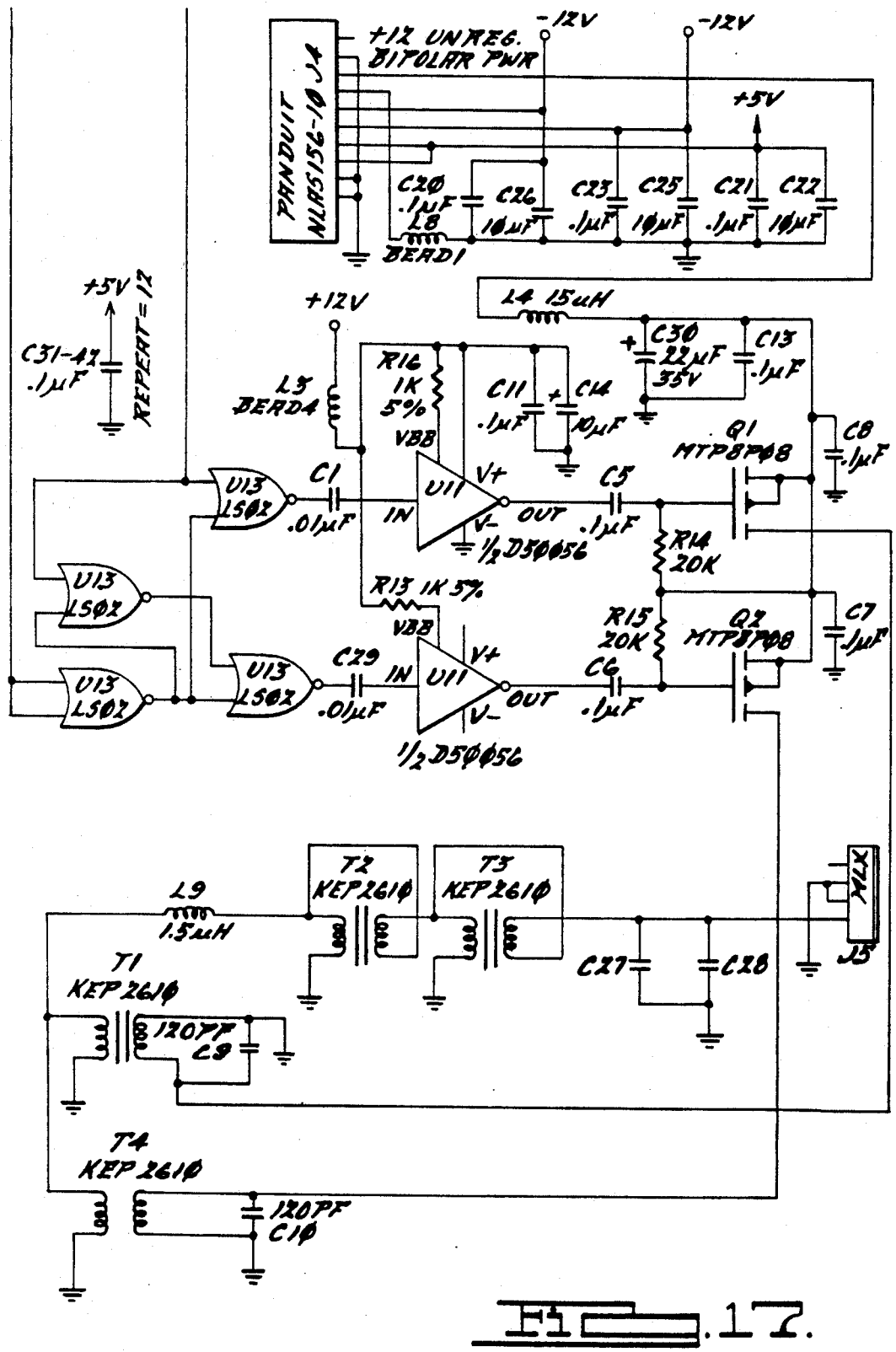

FIGS. 15, 16 and 17 depict the analog peripheral control circuitry which was designated generally by block 350 in FIG. 3. As noted above, many of the microsurgical implements are operated by fluid pressure signals. The control system console includes venturi pressure arrangement for providing the pneumatic signals used to control the surgical implements. The circuitry illustrated in FIGS. 15, 16 and 17 interfaces the microprocessor with the analog controlled valves (not shown) used to provide the specific pneumatic signals required by the surgical implements and by various pneumatically operated peripheral devices. In this regard, the presently preferred embodiment employs an illumination system with light dimming capabilities provided by a pneumatically controlled movable carriage. The analog peripheral control circuitry of FIGS. 15, 16 and 17 allow the microprocessor to control this light dimming device.

In addition, the cassette 100 for collecting aspiration fluids is also controlled by the analog circuitry. The cassette employs a light emitting diode and phototransistor pair for sensing the level of fluid within the cassette. This sensing mechanism provides an indication to the microprocessor of when the cassette is nearly full and needs to be replaced. The cassette is provided with a resilient-walled passageway which is blocked by squeezing action of a solenoid plunger operated by microprocessor 310. In addition to these functions, the analog circuitry also controls the BIPOLAR power used for cauterizing.

Referring more specifically to FIG. 15, the analog peripheral control circuitry couples to the microprocessor via the SYSAn and SYSDn system buses via jack J1. Interrupt requests from the analog devices are processed through logic gates U20 to provide interrupt request signal IRQ*. These two buses are buffered through buffers U4 and U5 while the interrupt request signals are buffered through U15. Referring to FIG. 16, which is a continuation of the schematic diagram of FIG. 15, the buffers U4 and U15 couple to the data bus D of the analog control circuitry, while buffer U5 couples to the address bus A of the analog control circuitry. The light dimming pneumatic controller is coupled to the control circuit via jack J2 and the cassette interface at jack J3. The BIPOLAR control circuitry is illustrated in FIG. 17.

In operation, the nurse or surgeon inserts cassette 100 into cassette slot 102, depressing it until it is locked into place. The act of sliding the cassette into place causes the aspiration vacuum system to be connected to the vacuum port of the cassette. The tubing for an aspiration instrument may then be inserted into the opening 148. At this time, the other surgical instruments are connected to the front panel couplers 40 as required. The fiber optic illumination instrument 214 is plugged into the fiber optic coupler 210. The system power switch 38 is then turned on, which causes powerup reset circuit 372 to reset microprocessor 310 after the appropriate time delay. In the presently preferred embodiment, the microprocessor controlled microcomputer system powers up in the initial function selection mode with the display screen 16 appearing as in FIG. 18. In this initial selection mode, only two of the switches 18a and 18b are active. The remaining push buttons and potentiometer knobs have no effect. In the screen region 22a, adjacent button 18a, appears the message "Anterior". In the screen region 22b, adjacent button 18b, appears the message "Posterior".

Figure 19:
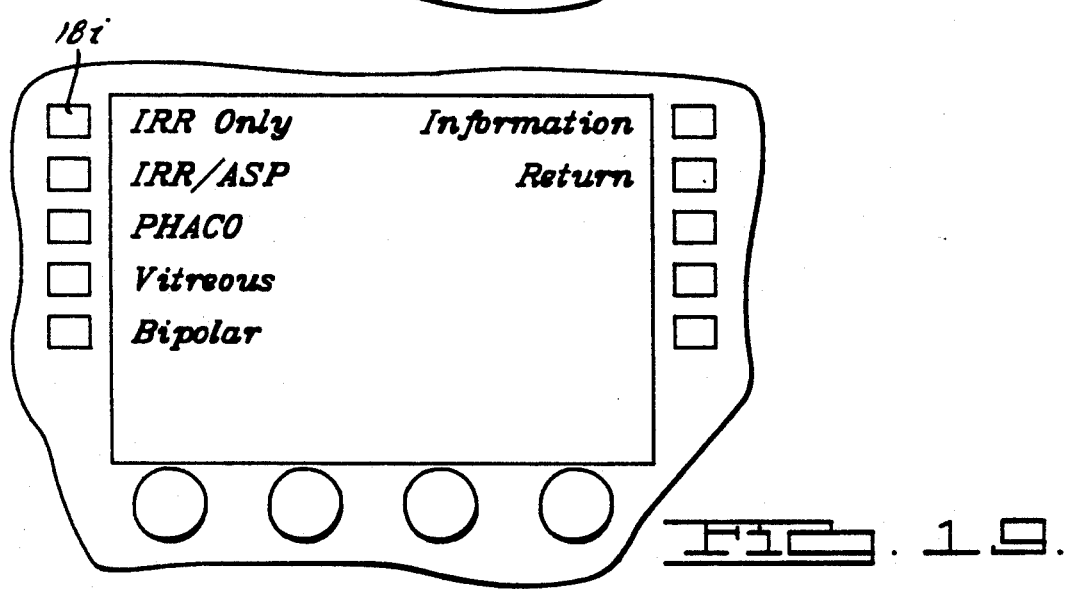

By depressing button 18a, the front panel display changes to display the anterior segment menu which provides the several different surgical procedures shown in FIG. 19. In addition to the surgical procedures offered on the menu, the user may also select information or help screens or the user may select return, which returns to the initial selection screen.

Figure 20:
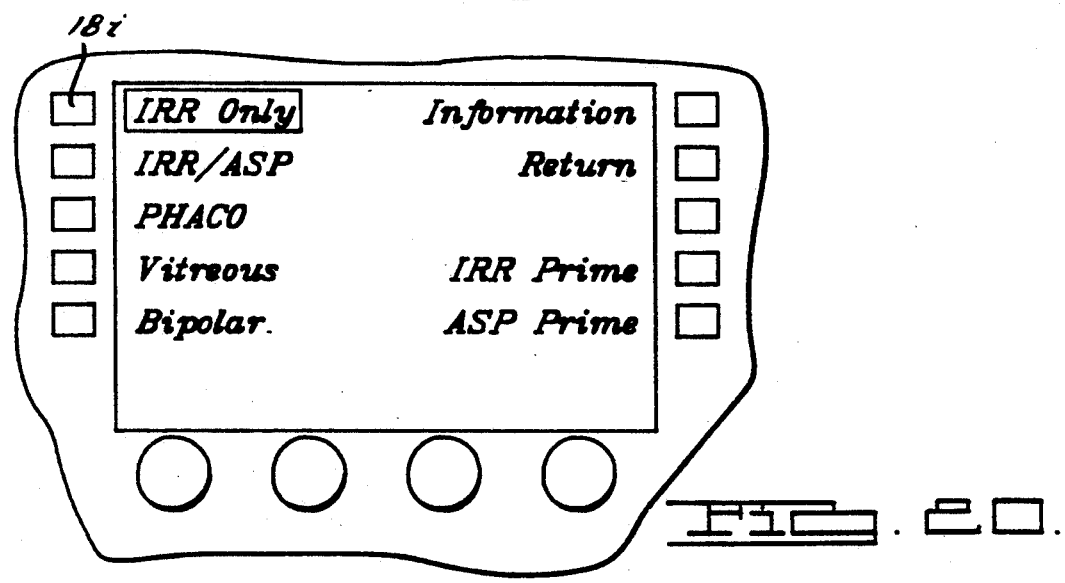
Figure 21:
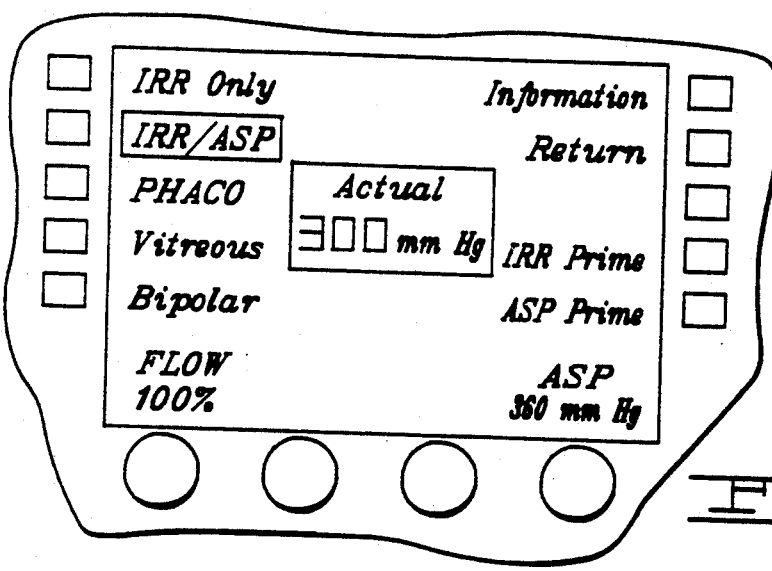
Figure 22:
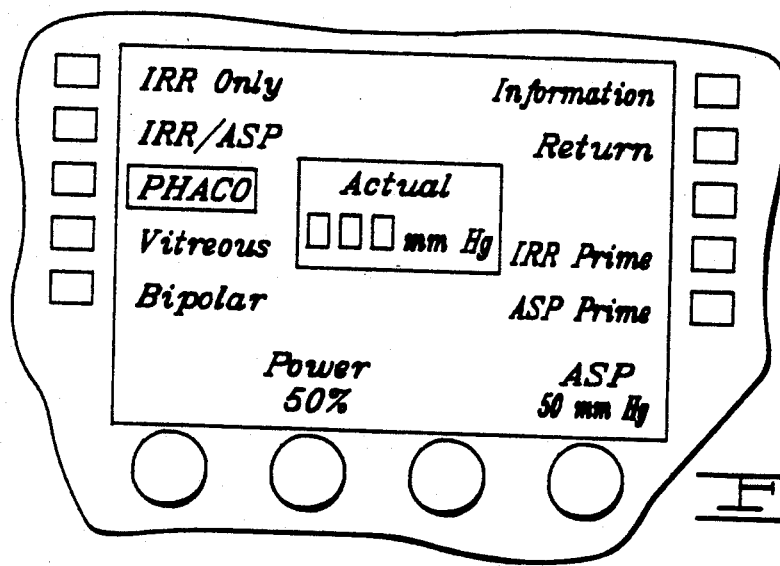
Figure 23:
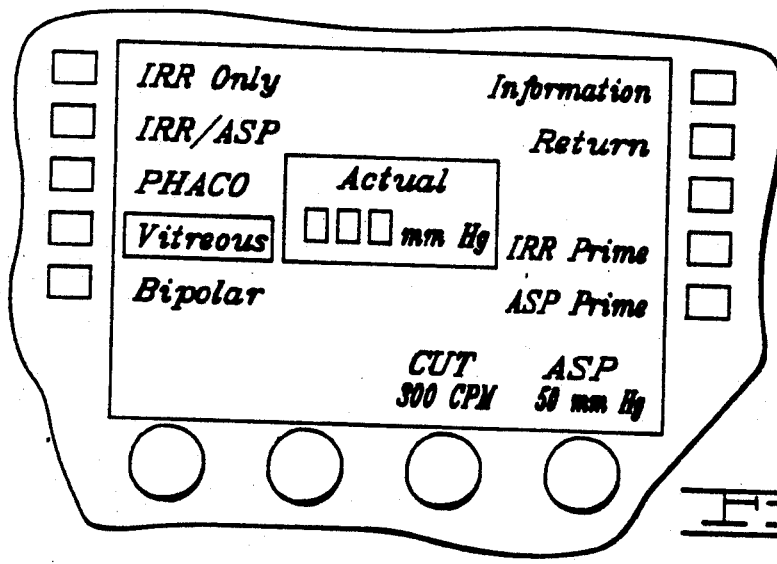
Figure 24:
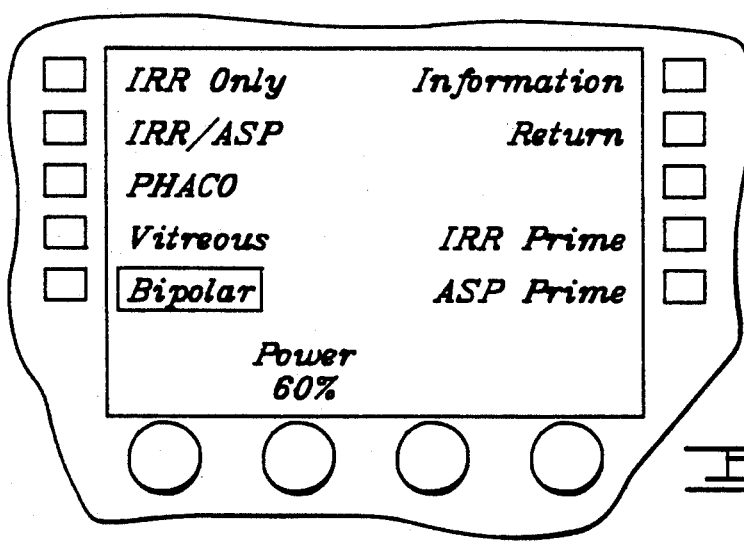
Figure 25:
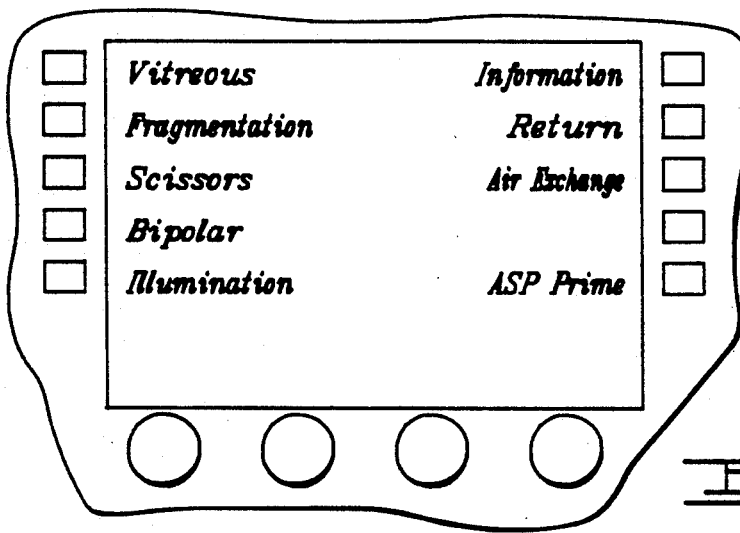
Figure 26:
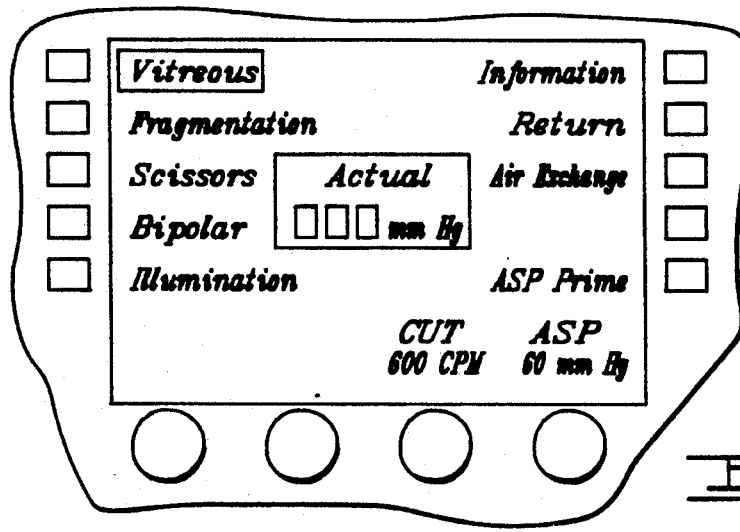
Figure 27:
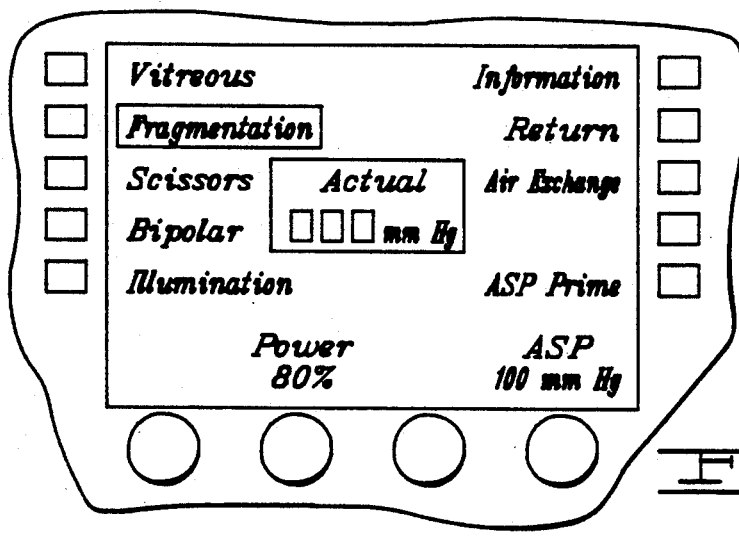
Figure 28:
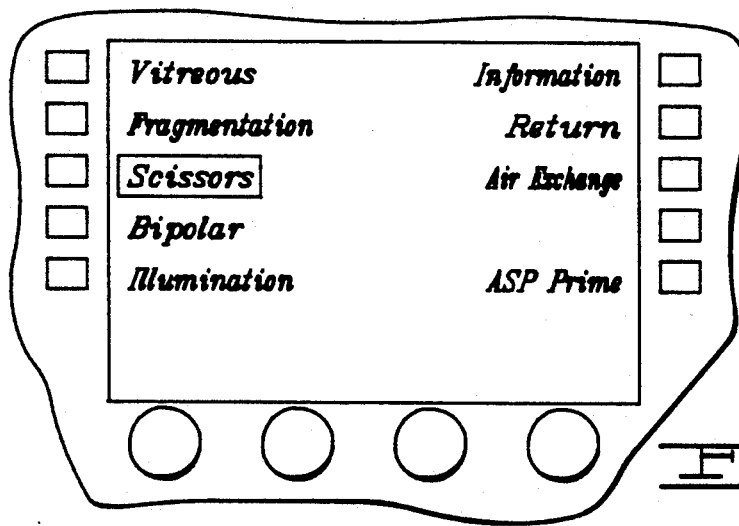
Figure 29:
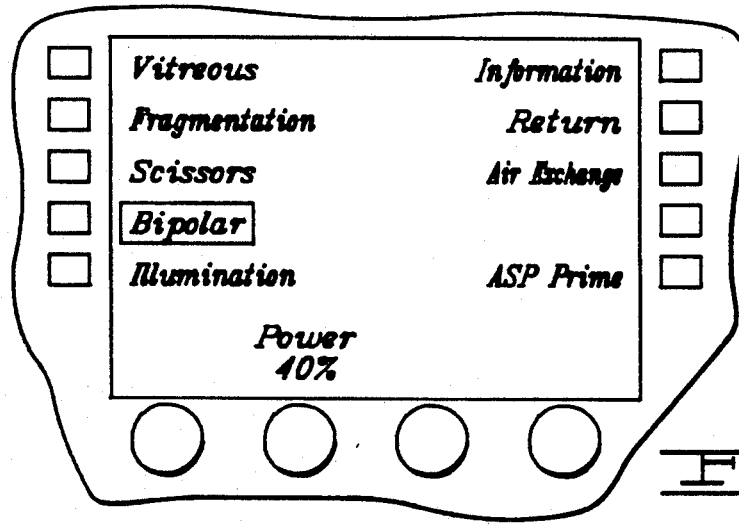
Figure 30:
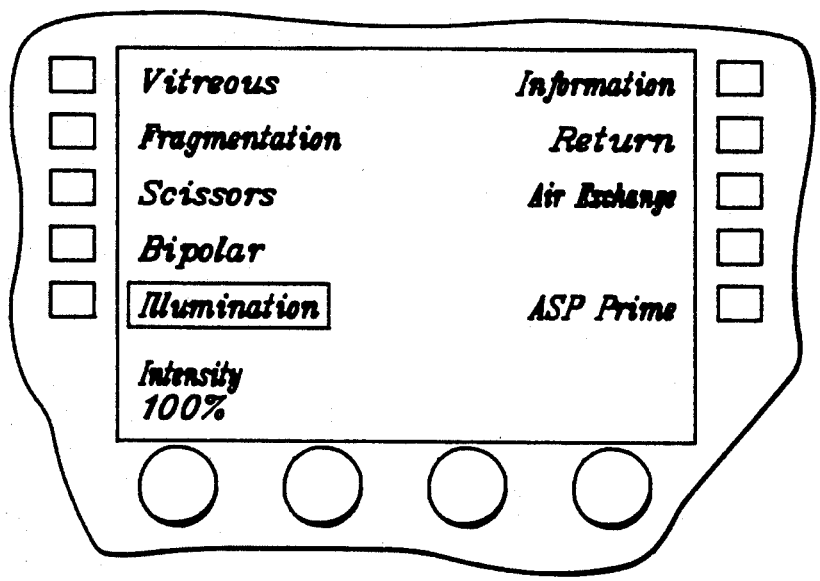
Figure 31:
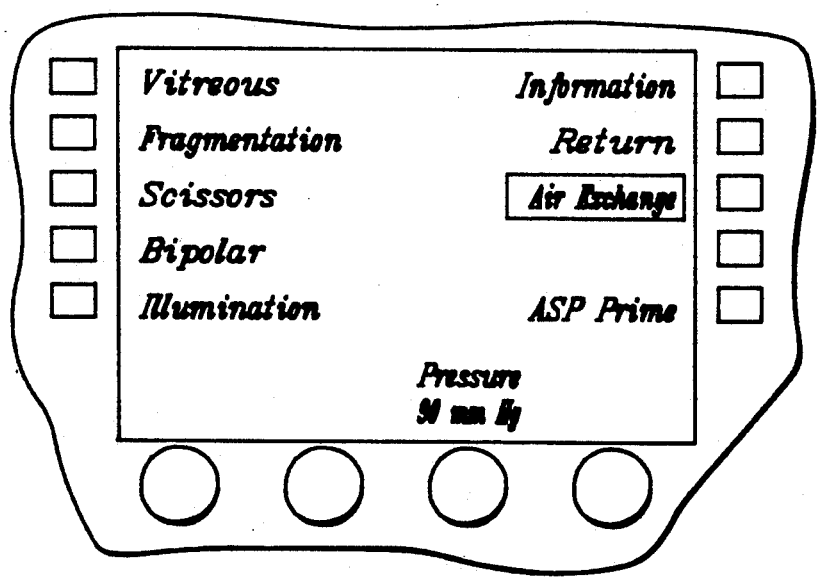

By pressing the button 18i adjacent the menu entry entitled "IRR ONLY", the screen displays a submenu which is illustrated in FIG. 20. This menu, in turn, offers other selections. Note that the IRR ONLY message is highlighted or emphasized in FIG. 20 and that two additional functions namely IRR PRIME and ASP PRIME, are added. FIGS. 21-24 illustrate the appearance of the display screen when the remaining selections are made from the menu of FIG. 19. With reference to FIGS. 21-24, it is seen that certain of the potentiometer knobs 20 have been made active and that adjacent each active knob there is a human readable indication of the function and current setting. In FIG. 23, for example, the cutting rate is indicated at 300 cpm, while the aspiration rate is indicated at 50 mmHg.

Also shown in the display screen in FIG. 23, is the message indicating the actual aspiration vacuum level, as opposed to the maximum setting provided by the ASP potentiometer knob.

Figure 18:
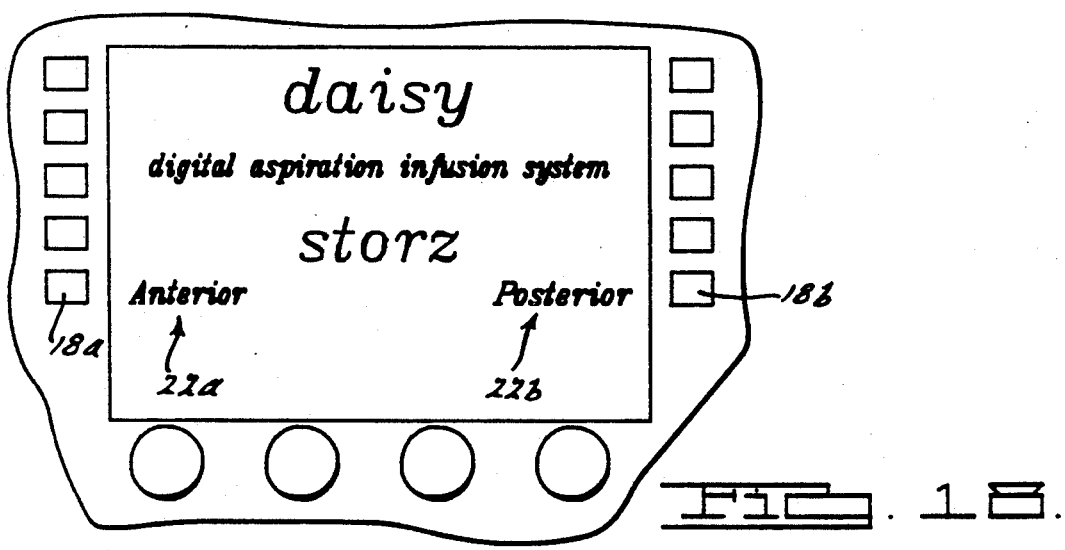
FIGS. 18-31 depict various menus displayable on the display screen of the invention.

The remaining Figures relate to other functions provided by the control system and various menu levels of procedures selected from the initial selection menu of FIG. 18.

From the foregoing, it will be seen that the menus displayed on the screen change depending upon the selections made by the user. While the menus illustrated are in the English language, the invention is capable of displaying these menus in other languages as well, using the bank switching techniques previously described. In addition, the particular default setting of cutting rate, aspiration vacuum, diathermy power, fragmentation power, etc. can be unique to each different surgeon who uses the control system, merely by inserting that surgeon's preprogrammed key into the jack on the system console.

While many of the functions are the same from menu to menu, certain groups of functions are mutually exclusive. The IRR ONLY, IRR/ASP and VITREOUS modes are mutually exclusive modes for the menu shown in FIG. 19. When one of these modes is in operation and a different one is selected, it automatically cancels the previous selection. Repressing the same mode switch a second time causes the mode to be cancelled. This allows other modes which may function simultaneously to be selected individually. For example, in the extracapsular mode, the user could select IRR ONLY and BIPOLAR allowing the foot pedal to control both of these functions. However, either function could be then eliminated by simply repressing its designated push button.

In the phacoemulsification mode, IRR ONLY, IRR/ASP, PHACO, and VITREOUS, FRAGMENTATION and SCISSORS are also mutually exclusive functions. BIPOLAR, ILLUMINATION and AIR EXCHANGE then become individually selected functions which can be used (in any combination) with one of those three principle functions, i.e. VIT, FRAG, and SCISSORS.

In all anterior segment procedures, both the IRR PRIME and ASP PRIME are illuminated. These allow the nurse or surgeon to reprime any of the lines without the need to access the surgeon's foot pedal. All posterior segment screens or menus, eliminate the IRR PRIME since continuous irrigation is generally used by the posterior segment surgeon.

The RETURN selection is continuously displayed to allow the user to traverse the menu screens without requiring the system to be shut off and reinitialized. The INFORMATION control button is a shift key which allows the user by depressing it to then select whichever mode's information is desired. For example, if the user is in the extracapsular mode of FIG. 19 and depresses the information button while also depressing the IRR ONLY button, information about the IRR ONLY mode will be displayed on the screen.

With respect to the posterior segment menus (e.g., FIGS. 25-31), the selection of FRAGMENTATION preferably automatically cancels BIPOLAR, ILLUMINATION and/or AIR EXCHANGE modes since these are not used in conjunction with the fragmenter. Returning to a SCISSORS or VITREOUS mode thereafter requires the reinitialization of any of these modes desired. Also whenever VITRECTOMY and AIR EXCHANGE are selected together, the CUT RATE display will be extinguished and the AIR PRESSURE display illuminated and controlled by the appropriate potentiometer knob. Under such circumstances, the cutter will continue to function normally. Should the user require a change in cutting rate, the AIR EXCHANGE control is simply turned off to eliminate the cutting rate display in order to access the appropriate knob. The AIR EXCHANGE function can then be reinitiated.

In addition to the front panel controls, the foot pedal is also capable of controlling certain of the functions. Table I below describes the foot pedal functions for different surgical modes.

TABLE I

| Mode | Left | Down | Right |
|---|---|---|---|
| Anterior (Extracap & Phaco) | | | |
| IRR ONLY | — | on/off | — |
| IRR/ASP | Reflux on/off, 1 cycle | IRR ONLY, linear aspiration | — |
| PHACO | Reflux on/off, 1 cycle | IRR, ONLY, linear aspiration | on/off (momentary) |
| VITREOUS | Reflux on/off, 1 cycle | IRR ONLY, cutting & linear aspiration | — |
| BIPOLAR | on/off (momentary) | — | — |
| Posterior | | | |
| VITREOUS | — | linear aspiration | on/off cutting (intermittent) |
| FRAGMENTATION | — | — | on/off fragmentation (momentary) |

TABLE I-continued

| Mode | Left | Down | Right |
|---|---|---|---|
| SCISSORS | — | proportion or speed | proportionate/multicut (intermittent) |
| BIPOLAR | on/off (momentary) | — | — |
| FIBER-OPTIC | — | — | — |
| AIR EXCHANGE | — | — | — |

While the invention has been described in connection with its presently preferred embodiment, it will be understood that the invention is capable of certain modification and change without departing from the spirit of the invention as set forth in the appended claims.

What is claimed is:

1. A microsurgical control system for controlling at least one ophthalmic microsurgical instrument for performing ophthalmic surgical procedures, the system comprising:
   a console;
   connecting means for connecting at least one ophthalmic microsurgical instrument to said console;
   control means coupled to said connecting means for providing a plurality of surgical procedure control signals to said instrument;
   a first controller for displaying human readable characters at least a first portion of which are displayed at a first set of predetermined areas of said console and a second portion of which are displayed at a second predetermined area on said console;
   a second controller adjacent one of said first and second predetermined areas of said console;
   a third controller adjacent the other of said first and second predetermined areas of said console;
   wherein at least one of said second and third controllers includes means for changing the human readable characters at a selected predetermined area; and
   means for selecting the predetermined area at which the human readable character display and the corresponding control signals is to be changed.

2. The invention according to claim 1 wherein each of said second and third controller comprises at least one switch.

3. The invention according to claim 2 wherein said means for selecting comprises one of said at least one switch positioned adjacent said one of said first and second predetermined areas.

4. A microsurgical control system for controlling at least one opthalmic microsurgical instrument for performing ophthalmic surgical procedures, the system comprising:
   a console;
   connecting means on said console for connecting to at least one ophthalmic microsurgical instrument;
   control means coupled to said connecting means for providing a plurality of surgical procedure control signals to said instrument; and
   a controller coupled to said control means for controlling said control signals to said instrument;
   said control means including means for defining predetermined and selectable surgical procedures, said defining means including at least one non-volatile, programmable memory circuit for storing a set of default operating values for controlling said instrument during performance of said surgical procedures;
   wherein said control means includes means for reprogramming at least one value of said set of default operating values; and
   wherein said defining means comprises last entry reactivating means for reproducing the last entered set of operating values as a default set of operating values.

* * * * *